(12) United States Patent
Amano et al.

(10) Patent No.: US 7,754,889 B2
(45) Date of Patent: Jul. 13, 2010

(54) OPTICALLY ACTIVE TRANSITION METAL-DIAMINE COMPOUND AND PROCESS FOR PRODUCING OPTICALLY ACTIVE ALCOHOL WITH THE SAME

(75) Inventors: Akira Amano, Kanagawa (JP); Daisuke Igarashi, Kanagawa (JP); Noboru Sayo, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 414 days.

(21) Appl. No.: 10/594,744

(22) PCT Filed: Mar. 28, 2005

(86) PCT No.: PCT/JP2005/005728
§ 371 (c)(1),
(2), (4) Date: Sep. 29, 2006

(87) PCT Pub. No.: WO2005/092830
PCT Pub. Date: Oct. 6, 2005

(65) Prior Publication Data
US 2007/0149831 A1 Jun. 28, 2007

(30) Foreign Application Priority Data
Mar. 29, 2004 (JP) .............................. 2004-096472

(51) Int. Cl.
*C07F 15/00* (2006.01)
(52) U.S. Cl. ...................... 548/101; 556/136
(58) Field of Classification Search ................. 548/101; 556/136
See application file for complete search history.

(56) References Cited

U.S. PATENT DOCUMENTS 5,274,146 A 12/1993 Ishizaki et al.
5,324,861 A 6/1994 Ishizaki et al.

FOREIGN PATENT DOCUMENTS

JP 07-000716 1/1995

OTHER PUBLICATIONS

Kise et al. "Reductive coupling of aromatic oxims and azines to 1,2-diamines using Zn-MsOH or Zn-TiCl4" Tetrahedron Letters, 2001, vol. 42, Iss 12, pp. 2365-2368.*
Jennerwein et al. "Influence of ring substituents on the antitumor effect of dichloro(1,2-diphenylethylenediamine)platinum(II) complexes" J Cancer Res Clin Oncol, 1988, vol. 114, pp. 347-358.*
Hashiguchi et al. "Asymmetric Transfer Hydrogenation of Aromatic Ketones Catalyzed by Chiral Ruthenium(II) Complexes" Journal of the American Chemical Society, 1995, vol. 117, pp. 7562-7563.*
Warad et al. "Supported organometallic complexes part 39: cationic diamine(ether-phosphine)ruthenium(II) complexes as precursors for the hydrogenation of trans-4-phenyl-3-butene-2-one" Inorganica Chemica Acta, 2004, vol. 357, pp. 1847-1853.*
Kise et al., Tetrahedron Letters, 42(12):2365-2368 (2001).
Liao et al., Synthetic Communications, 27(9):1483-1486 (1997).
Pandey et al., Indian Journal of Chemistry, 21B(5):467-470 (1982).
Jennerwein et al., Journal of Cancer Research and Clinical Oncology, 114(4):347-358 (1988).
Schneider et al., Journal of the Chemical Society, Chemical Communications, 6:490-491 (1992).
G. Zassinovich et al., "Asymmetric Hydrogen Transfer Reactions Promoted by Homogeneous Transition Metal Catalysts", Chem. Rev., vol. 92, pp. 1051-1069 (1992).
S. Hashiguchi et al., "Asymmetric Transfer Hydrogenation of Aromatic Ketones Catalyzed by Chiral Ruthenium (II) Complexes", J. Am. Chem. Soc., vol. 117, pp. 7562-7563 (1995).
N. Uematsu et al., "Asymmetric Transfer Hydrogenation of Imines", J. Am. Chem. Soc., vol. 118, pp. 4916-4917 (1996).
T. Thorpe et al., "Efficient rhodium and iridium-catalysed asymmetric transfer hydrogenation using water-soluble aminosulfonamide ligands", Tetrahedron Letters, vol. 42, pp. 4041-4043 (2001).

* cited by examiner

*Primary Examiner* — Joseph R Kosack
(74) *Attorney, Agent, or Firm* — Peter F. Corless; Christine C. O'Day; Edwards Angell Palmer & Dodge LLP

(57) ABSTRACT

The present invention provides a water-soluble transition metal-diamine complex which can be easily separated from reaction products through liquid separation, etc. and is recycleable; an optically active diamine compound constituting the ligand of the complex; and a catalyst for asymmetric synthesis which comprises these. The present invention relates to a water-soluble optically active transition metal-diamine complex represented by the formula (2):

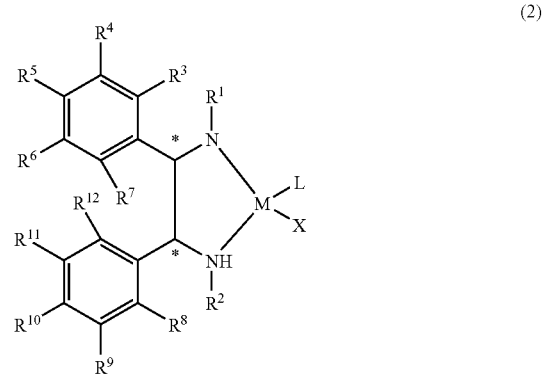

(2)

[wherein $R^1$ and $R^2$ each represents hydrogen, a hydrocarbon group, —$SO_2R^{13}$ (wherein $R^{13}$ is a hydrocarbon group, substituted amino, etc.), etc.; $R^3$ to $R^{12}$ each represents hydrogen, a hydrocarbon group, alkoxy, substituted amino, etc.; M represents a transition metal; X represents halogen; L represents a ligand; and * indicates an asymmetric carbon atom; provided that at least one of $R^3$ to $R^7$ and $R^8$ to $R^{12}$ is substituted amino], a catalyst for asymmetric synthesis containing the complex, and a process for producing an optically active alcohol, which comprises using the catalyst to asymmetrically reduce a ketone.

17 Claims, No Drawings

OPTICALLY ACTIVE TRANSITION METAL-DIAMINE COMPOUND AND PROCESS FOR PRODUCING OPTICALLY ACTIVE ALCOHOL WITH THE SAME

BACKGROUND OF THE INVENTION

1. Field of the Invention

The present invention relates to an optically active transition metal-diamine complex useful as a catalyst for various asymmetric organic synthesis reactions, etc., or the like, and a process for producing an optically active alcohol with the same.

2. Description of the Related Art

Hitherto, many transition metal complexes have been used as catalysts for organic metal reactions. In particular, because novel metal complexes are highly active, stable and easy to handle although they are expensive, many synthesis reactions using novel metal complexes as a catalyst have been developed, inter alia, there is a remarkable development in asymmetric synthesis reactions using an asymmetric complex as a catalyst. There have been made a large number of reports on an improvement of the efficiency of organic synthesis reaction which was inefficient with conventional means.

Among these reactions, asymmetric reactions using an asymmetric complex having an optically active phosphine ligand as a catalyst have been very widely developed, and some of them have been industrialized. Also, for example, there are many complexes, wherein a transition metal such as ruthenium, rhodium and iridium is coordinated with an optically active nitrogen compound, having excellent performances as a catalyst for asymmetric synthesis reactions. In order to improve the performances of the catalysts, a great number of optically active nitrogen compounds having a special structure have been developed so far (Non-patent Document 1 and so on).

For example, Non-patent Documents 2 and 3 report complexes wherein ruthenium is coordinated with optically active N-p-toluenesulfonyl-1,2-diphenylethylenediamine as a ligand. However, any reaction using this ligand is conducted in an organic solvent, and there has not been reported any example wherein the reaction is conducted only in water. When productions of pharmaceutical intermediates or the like are attempted by methods described therein, the resultant intermediate is not easily separated from the intermediate and the catalyst by operation such as distillation since many of these intermediates are in a solid form.

As described above, the separation of a catalyst and a product is one of the unavoidable problem. In particular, in homogeneous catalyst reactions, the catalyst used therein is easily dissolved in the organic layer therein; therefore, in order to separate the catalyst and the product, a complicated method such as distillation, recrystallization and the like is necessary.

For example, Patent Document 1 discloses an asymmetric hydrogenation using a sulfonated-BINAP. However, the document does not disclose any method for recovering a catalyst dissolved in water or reuse thereof after the hydrogenation.

Non-patent Document 4 reports a transfer hydrogenation type reduction using a ligand wherein the phenyl group of benzenesulfonyl-1,2-diaminocyclohexane is sulfonated at the para-position. The reaction, however, is conducted in a solvent of isopropanol-water. It is, therefore, necessary that a product therein is separated by distillation.

One method for solving such a problem of separation of a product and a catalyst would be a method of using a water-soluble catalyst to conduct a reaction in a solvent system containing water. In this case, the resultant product is dissolved in the organic layer therein and the catalyst is dissolved in the water layer. It therefore appears that the catalyst can easily be separated only by extraction operation. Non-patent Document 5, for example, describes a process for producing 1,2-bis(4-N,N-dimethylaminophenyl)ethylenediamine as a water-soluble amines, which is a racemic form. However, Non-patent Document 5 does not describe any optically active substance of the diamine, and the document neither describes any example of production of an optically active transition metal-diamine complex using above diamine as a ligand nor the use of said optically active transition metal-diamine complex as a catalyst for asymmetric hydrogenation. Also, Non-patent Document 6 describes 1,2-bis(4-N,N-dimethylaminophenyl)ehylenediamine and dichloro(1,2-bis(4-N,N-dimethylaminophenyl)ehylenediamine) platinum (II) complex which are racemic forms, and anticancer effect by use of said platinum complex. However, Non-patent Document 6 neither describes any optically active substances of the diamine nor the platinum complex, and the document also does not describe the use of the platinum catalyst as a catalyst for asymmetric hydrogenation.

Patent Document 1: JP-A-H05-170780

Non-patent Document 1: Chem Rev., 92, 1051-1069 (1992)

Non-patent Document 2: J. Am. Chem. Soc., vol. 117, 7562-7563 (1995)

Non-patent Document 3: J. Am. Chem. Soc., vol. 118, 4916-4917 (1996)

Non-patent Document 4: Tetrahedron Lett., vol. 42, 4041-4043 (2001)

Non-patent Document 5: Tetrahedron Lett., vol. 42, 2365-2368 (2001)

Non-patent Document 6: J. Cancer Res. Clin. Oncol., 114, 347-358 (1998)

DISCLOSURE OF THE INVENTION

Under such circumstances, it has been desired to develop a water-soluble catalyst which enables to recover an expensive novel metal catalyst selectively and easily from a reaction mixture. If the catalyst can be recovered easily, the catalyst can be reused and further, from the viewpoint of environment pollution, a clean chemical reaction can be conducted.

The present invention has been accomplished in view of the above-mentioned problems. For example, when the catalyst of the present invention is used as a catalyst for asymmetric reduction to conduct an asymmetric reduction of a prochiral ketone, a desired optically active alcohol can be obtained with a high yield and a good optical purity. Not only that, the catalyst can be used in an aqueous solvent, and further the catalyst can easily be separated from the reaction product after the reaction by liquid separation, extraction or the like. An object of the present invention is to provide such a recyclable water-soluble transition metal-diamine complex.

The present invention relates to an optically active diamine compound represented by the formula (1):

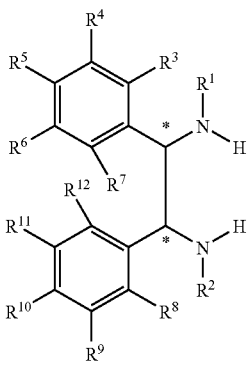

(1)

wherein $R^1$ and $R^2$ each independently represent a hydrogen atom, an optionally substituted hydrocarbon group, or —$SO_2R^{13}$ (wherein $R^{13}$ represents an optionally substituted hydrocarbon group, a camphoryl group, or a substituted amino group), $R^3$ to $R^{12}$ each independently represent a hydrogen atom, an optionally substituted hydrocarbon group, an optionally substituted heterocyclic group, an optionally substituted alkoxy group, an optionally substituted aryloxy group, an optionally substituted aralkyloxy group, or a substituted amino group, and * represents an asymmetric carbon atom, provided that at least one of $R^3$ to $R^7$ and $R^8$ to $R^{12}$ is the substituted amino group.

The present invention also relates to an optically active transition metal-diamine complex represented by the formula (2):

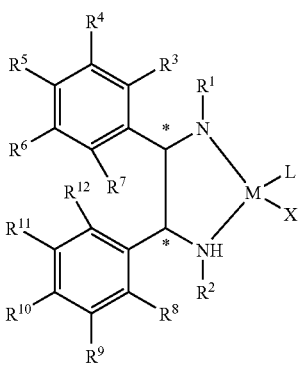

(2)

wherein $R^1$ and $R^2$ each independently represent a hydrogen atom, an optionally substituted hydrocarbon group, or —$SO_2R^{13}$ (wherein $R^{13}$ represents an optionally substituted hydrocarbon group, a camphoryl group, or a substituted amino group), $R^3$ to $R^{12}$ each independently represent a hydrogen atom, an optionally substituted hydrocarbon group, an optionally substituted heterocyclic group, an optionally substituted alkoxy group, an optionally substituted aryloxy group, an optionally substituted aralkyloxy group, or a substituted amino group, M represents a transition metal, X represents a halogen atom, L represents a ligand, and * represents an asymmetric carbon atom, provided that at least one of $R^3$ to $R^7$ and $R^8$ to $R^{12}$ is the substituted amino group.

The present invention further relates to an optically active transition metal-diamine complex obtained by reacting an optically active diamine compound represented by the following formula (1):

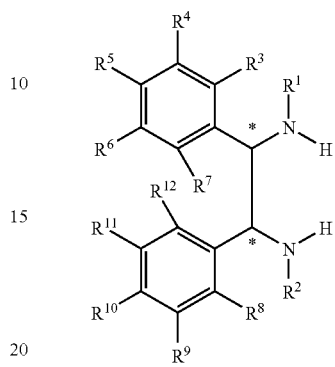

(1)

wherein $R^1$ and $R^2$ each independently represent a hydrogen atom, an optionally substituted hydrocarbon group, or —$SO_2R^{13}$ (wherein $R^{13}$ represents an optionally substituted hydrocarbon group, a camphoryl group, or a substituted amino group), $R^3$ to $R^{12}$ each independently represent a hydrogen atom, an optionally substituted hydrocarbon group, an optionally substituted heterocyclic group, an optionally substituted alkoxy group, an optionally substituted aryloxy group, an optionally substituted aralkyloxy group, or a substituted amino group, and * represents an asymmetric carbon atom, provided that at least one of $R^3$ to $R^7$ and $R^8$ to $R^{12}$ is the substituted amino group; and a transition metal compound represented by the formula (3):

$$[MX_mL_n]_p \quad (3)$$

wherein M represents a transition metal, X represents a halogen atom, L represents a ligand, m represents 2 or 3, n represents 0 or 1, and p represents 1 or 2.

Furthermore, the present invention relates to a catalyst for asymmetric synthesis comprising any one of the above-mentioned optically active transition metal-diamine complexes.

The present invention also relates to a catalyst for asymmetric synthesis comprising an optically active diamine compound represented by the formula (1):

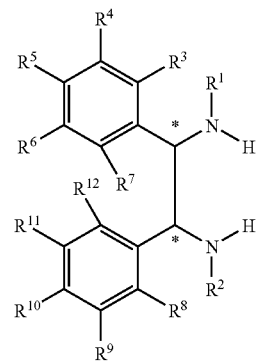

(1)

wherein $R^1$ and $R^2$ each independently represent a hydrogen atom, an optionally substituted hydrocarbon group, or —SO₂R¹³ (wherein R¹³ represents an optionally substituted hydrocarbon group, a camphoryl group, or a substituted amino group), R³ to R¹² each independently represent a hydrogen atom, an optionally substituted hydrocarbon group, an optionally substituted heterocyclic group, an optionally substituted alkoxy group, an optionally substituted aryloxy group, an optionally substituted aralkyloxy group, or a substituted amino group, and * represents an asymmetric carbon atom, provided that at least one of R³ to R⁷ and R⁸ to R¹² is the substituted amino group; and a transition metal compound represented by the formula (3):

[MX$_m$L$_n$]$_p$  (3)

wherein M represents a transition metal, X represents a halogen atom, L represents a ligand, m represents 2 or 3, n represents 0 or 1, and p represents 1 or 2.

The present invention further relates to a process for producing an alcohol, more specifically an optically active alcohol, which comprises subjecting a ketone, more specifically a prochiral ketone to an asymmetric reduction in an aqueous solvent in the presence of the above-mentioned catalyst for asymmetric synthesis of the present invention.

More specifically, the present invention relates to a process for producing an optically active alcohol represented by the formula (5):

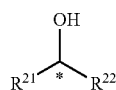

(5)

wherein * represents an asymmetric carbon atom, R²¹ and R²² each independently represent an optionally substituted hydrocarbon group, an optionally substituted heterocyclic group, or a ferrocenyl group, provided that R²¹≠R², and R²¹ and R²² may be bonded to each other to form a cyclic ketone having a substituent; characterized by reacting a ketone represented by the formula (4):

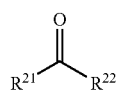

(4)

wherein R²¹ and R²² are the same as described above; to an asymmetric reduction, more specifically asymmetric transfer hydrogenation in an aqueous solvent in the presence of the above-mentioned catalyst for asymmetric synthesis of the present invention.

Furthermore, the present invention relates to a process for producing the above-mentioned alcohol, more specifically optically active alcohol characterized by using the catalyst for asymmetric synthesis (catalyst for asymmetric reduction) which is recycled after use.

The present invention also relates to a diamine compound represented by the formula (1b):

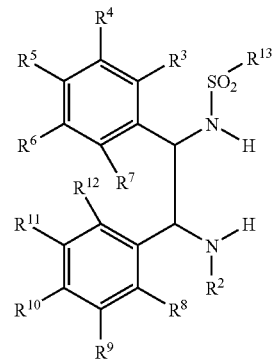

(1b)

wherein R² represents a hydrogen atom, an optionally substituted hydrocarbon group, or —SO₂R¹³ (wherein R¹³ represents an optionally substituted hydrocarbon group, a camphoryl group, or a substituted amino group), R³ to R¹² each independently represent a hydrogen atom, an optionally substituted hydrocarbon group, an optionally substituted heterocyclic group, an optionally substituted alkoxy group, an optionally substituted aryloxy group, an optionally substituted aralkyloxy group, or a substituted amino group, and R¹³ represents an optionally substituted hydrocarbon group, a camphoryl group, or a substituted amino group, provided that at least one of R³ to R⁷ and R⁸ to R¹² is a substituted amino group.

The present invention further relates to use of the diamine compound of the present invention represented by the above-mentioned formula (1b) as a ligand in a metal complex. Furthermore, the present invention relates to use of the diamine compound represented by the above-mentioned formula (1b) as a catalyst component or a ligand for a catalyst in asymmetric synthesis reaction, more specifically asymmetric reduction.

That is, the present inventors have made considerable studies with respect to transition metal complexes which are water-soluble and can easily be recovered and recycled, consequently found that the above-mentioned problems are solved by conducting asymmetric reduction of a prochiral ketone by use of an optically active transition metal-diamine complex having, as a ligand, an optically active diamine compound represented by the formula (1) as a catalyst for asymmetric reduction such as a catalyst for asymmetric hydrogenatoin or a catalyst for asymmetric transfer hydrogenation, so that a desired optically active alcohol can be obtained with a good yield and a good optical purity. Thus, the present invention has been accomplished.

The optically active transition metal-diamine complex of the present invention is characterized by having, as a ligand, an optically active diamine compound wherein a phenyl group has a substituted amino group. The optically active transition metal-diamine complex of the present invention has activity as a catalyst for reduction, and further the whole catalyst becomes water-soluble so that a novel water-soluble catalyst can be provided.

In the above-mentioned formulae (1) and (2) and other formulae, the optionally substituted hydrocarbon group represented by R¹ and R² may be a hydrocarbon group and a substituted hydrocarbon group.

The hydrocarbon group may be a hydrocarbon group having 1 to 20 carbon atom(s), preferably 1 to 15 carbon atoms, more preferably 1 to 10 carbon atom(s), and examples thereof include an alkyl group, an alkenyl group, an alkynyl group, an alkadienyl group, an aryl group, an aralkyl group and the like.

The alkyl group may be linear, branched or cyclic, and includes, for example, an alkyl group having 1 to 20 carbon atom(s), preferably 1 to 15 carbon atom(s), more preferably 1 to 10 carbon atom(s). Specific examples thereof include, for example, methyl, ethyl, n-propyl, 2-propyl, n-butyl, 2-butyl, isobutyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, tert-hexyl, 2-methylpentyl, 3-methylpentyl, 4-methylpentyl, 2-methylpentane-3-yl, heptyl, octyl, nonyl, decyl, lauryl, steary, cyclopropyl, cyclobutyl, cyclopentyl, cyclohexyl, and the like.

The alkenyl group may be linear, branched or cyclic, and includes, for example, an alkenyl group having 2 to 20 carbon atoms, preferably 2 to 15 carbon atoms, more preferably 2 to 10 carbon atoms, further preferably 2 to 6 carbon atoms. Specific examples thereof include, for example, ethenyl, propenyl, 1-butenyl, pentenyl, hexenyl, heptenyl, octenyl, nonenyl, decenyl, and the like.

The alkynyl group may be linear or branched, and includes, for example, an alkynyl group having 2 to 20, preferably 2 to 15 carbon atoms, more preferably 2 to 10 carbon atoms, further preferably 2 to 6 carbon atoms. Specific examples thereof include, for example, ethynyl, 1-propynyl, 2-propynyl, 1-butynyl, 3-butynyl, pentynyl, hexynyl, and the like.

The alkadienyl group may have two double bonds in the chain of the above-mentioned alkyl group; and may be linear, branched or cyclic and includes, for example, an alkadienyl group having 4 or more carbon atoms, preferably 4 to 20 carbon atoms, more preferably 4 to 15 carbon atoms, further preferably 4 to 10 carbon atoms. Specific examples thereof include, for example, 1,3-butadienyl, 2,4-butadienyl, 2,3-dimethyl-1,3 butadienyl, and the like.

The aryl group includes, for example, an aryl group having 6 to 20 carbon atoms, preferably 6 to 15 carbon atoms, and the specific examples thereof include phenyl, naphthyl, anthryl, biphenyl, and the like.

The aralkyl group includes, for example, an aralkyl group, wherein at least one hydrogen atom in the above-mentioned alkyl group is substituted with the above-mentioned aryl group, having 7 to 20 carbon atoms, preferably 7 to 15 carbon atoms. Specific examples thereof include, for example, benzyl, 2-phenylethyl, 1-phenylpropyl, 3-naphthylpropyl, and the like.

The substituted hydrocarbon group (the hydrocarbon group having a substituent) may be a hydrocarbon group wherein at least one hydrogen atom in the above-mentioned hydrocarbon group is substituted with a substituent, and examples thereof include, for example, a substituted alkyl group, a substituted alkenyl group, a substituted alkynyl group, a substituted alkadienyl group, a substituted aryl group, a substituted aralkyl group, and the like.

The substituent may be an optionally substituted hydrocarbon group, a halogen atom, a halogenated hydrocarbon group, an optionally substituted alkoxy group, an optionally substituted aryloxy group, an optionally substituted aralkyloxy group, a substituted amino group, a nitro group, a cyano group, and the like.

The optionally substituted hydrocarbon group as the substituent is same as the above-mentioned optionally substituted hydrocarbon group.

The halogen atom as the substituent includes fluorine, chlorine, bromine, iodine atoms, and the like.

The halogenated hydrocarbon group as the substituent may be a hydrocarbon group wherein at least one hydrogen atom in the above-mentioned hydrocarbon group is substituted with the above-mentioned halogen atom. A preferred example of the halogenated hydrocarbon group includes, for example, a halogenated alkyl group. A preferred example of the halogenated alkyl group includes, for example, a halogenated alkyl group having 1 to 10 carbon atoms. Specific examples thereof include, for example, chloromethyl, bromomethyl, 2-chloroethyl, 3-bromopropyl, fluoromethyl, fluoroethyl, fluoropropyl, fluorobutyl, fluoropentyl, fluorohexyl, fluoroheptyl, fluorooctyl, fluorononyl, fluorodecyl, difluoromethyl, difluoroethyl, fluorocyclohexyl, trifluoromethyl, 2,2,2-trifluoroethyl, 3,3,3-trifluoropropyl, pentafluoroethyl, 3,3,4,4,4-pentafluorobutyl, perfluoro-n-propyl, perfluoroisopropyl, perfluoro-n-butyl, perfluoroisobutyl, perfluoro-tert-butyl, perfluoro-sec-butyl, perfluoropentyl, perfluoroisopentyl, perfluoro-tert-pentyl, perfluoro-n-hexyl, perfluoroisohexyl, perfluoroheptyl, perfluorooctyl, perfluorononyl, perfluorodecyl, 2-perfluorooctylethyl, perfluorocyclopropyl, perfluorocyclopentyl, perfluorocyclohexyl, and the like.

The optionally substituted alkoxy group as the substituent include an alkoxy group and a substituted alkoxy group. The alkoxy group may be linear, branched or cyclic, and includes, for example, an alkoxy group having 1 to 10 carbon atom(s), preferably 1 to 6 carbon atom(s). Specific examples thereof include, for example, methoxy, ethoxy, n-propoxy, 2-propoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methypentyloxy, 5-methylpentyloxy, cyclohexyloxy, and the like.

The substituted alkoxy group (the alkoxy group having a substituent) may be an alkoxy group wherein at least one hydrogen atom in the above-mentioned alkoxy group is substituted with the above-mentioned substituent.

The optionally substituted aryloxy group as the substituent includes aryloxy and substituted aryloxy groups. The aryloxy group includes, for example, an aryloxy group having 6 to 14 carbon atoms, and specific examples thereof include, for example, phenoxy, naphthyloxy, anthryloxy, and the like.

The substituted aryloxy group (the aryloxy group having a substituent) may be an aryloxy group wherein at least one hydrogen atom in the above-mentioned aryloxy group is substituted with the above-mentioned substituent.

The optionally substituted aralkyloxy group as the substituent includes an aralkyloxy group and a substituted aralkyloxy group. The aralkyloxy group includes, for example, an aralkyloxy group having 7 to 12 carbon atoms, and specific examples thereof include, for example, benzyloxy, 2-phenethyloxy, 1-phenylpropoxy, 2-phenylpropoxy, 3-phenylpropoxy, 1-phenylbutoxy, 2-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, 6-phenylhexyloxy, and the like.

The substituted aralkyloxy group (the aralkyloxy group having a substituent) may be an aralkyloxy group wherein at least one hydrogen atom in the above-mentioned aralkyloxy group is substituted with the above-mentioned substituent.

The substituted amino group as the substituent may be a chain or cyclic amino group wherein one or two hydrogen atom(s) in an amino group are substituted with one or two substituent(s) such as an amino protective group and the like. As the amino protective group as the substituent of the substituted amino group, any amino protective group that is ordinarily used as an amino protective group can be used.

Examples thereof include, for example, groups described as amino protective groups in "PROTECTIVE GROUPS IN ORGANIC SYNTHESIS THIRD EDITION (JOHN WILEY & SONS, INC. (1999))". Specific examples of the amino protective group include, for example, an alkyl group, an aryl group, an aralkyl group, an acyl group, an alkoxycarbonyl group, an aryloxycarbonyl group, an aralkyloxycarbonyl group, a substituted sulfonyl group, and the like.

The alkyl group, the aryl group and the aralkyl group for the above-mentioned amino protective group are the same as the respective groups as described in the above-mentioned hydrocarbon group.

The acyl group may be linear, branched or cyclic, and includes, for example, an acyl group having 1 to 20 carbon atom(s) and derived from a carboxylic acid such as an aliphatic carboxylic acid or an aromatic carboxylic acid and the like, and examples of said acyl group include alkylcarbonyl groups having 1 to 20 carbon atom(s), cycloalkylcarbonyl groups having 3 to 20 carbon atoms, cycloalkylalkylcarbonyl groups having 4 to 20 carbon atoms, arylcarbonyl groups having 6 to 20 carbon atoms, and aralkylcarbonyl groups having 7 to 20 carbon atoms. Specific examples thereof include, for example, formyl, acetyl, propionyl, butyryl, pivaloyl, pentanoyl, hexanoyl, lauroyl, stearoyl, benzoyl, and the like.

The alkoxycarbonyl group may be linear, branched or cyclic, and includes, for example, an alkoxycarbonyl group having 2 to 20 carbon atoms. Specific examples thereof include methoxycarbonyl, ethoxycarbonyl, n-propoxycarbonyl, 2-propoxycarbonyl, n-butoxycarbonyl, tert-butoxycarbonyl, pentyloxycarbonyl, hexyloxycarbonyl, 2-ethylhexyloxycarbonyl, lauryloxycarbonyl, stearyloxycarobnyl, cyclohexyloxycarbonyl, and the like.

The aryloxycarbonyl group includes, for example, an aryloxycarbonyl group having 7 to 20 carbon atoms, and specific examples thereof include phenoxycarbonyl, naphthyloxycarbonyl, and the like.

The aralkyloxycarbonyl group includes, for example, an aralkyloxycarbonyl group having 8 to 20 carbon atoms, and specific examples thereof include benzyloxycarbonyl, phenetyloxycarbonyl, 9-fluorenylmethyloxycarbonyl, and the like.

The substituted sulfonyl group includes, for example, a substituted sulfonyl group represented by $R^a$—$SO_2$— (wherein $R^a$ represents an optionally substituted hydrocarbon group or a substituted amino group).

The optionally substituted hydrocarbon group and the substituted amino group represented by $R^a$ are the same as the above-mentioned respective groups.

Specific examples of the substituted sulfonyl group include, for example, methanesulfonyl, trifluoromethanesulfonyl, benzenesulfonyl, p-toluenesulfonyl, camphorsulfonyl, —$SO_2N(CH_3)_2$ groups, and the like.

Specific examples of the amino group substituted with the alkyl group, that is, an alkyl-substituted amino group include, for example, mono- or di-alkylamino groups such as N-methylamino, N,N-dimethylamino, N,N-diethylamino, N,N-diisopropylamino, N-cyclohexylamino, and the like.

Specific examples of the amino group substituted with the aryl group, that is, an aryl-substituted amino group include, for example, mono- or di-arylamino groups such as N-phenylamino, N,N-diphenylamino, N-naphthylamino, N-naphthyl-N-phenylamino, and the like.

Specific examples of the amino group substituted with the aralkyl group, that is, an aralkyl-substituted amino group include, for example, mono- or di-aralkylamino groups such as N-benzylamino, N,N-dibenzylamino, and the like.

Specific examples of the amino group substituted with the acyl group include, that is, an acylamino group include, for example, formylamino, acetylamino, propionylamino, pivaroylamino, pentanoylamino, hexanoylamino, benzoylamino, and the like.

Specific examples of the amino group substituted with the alkoxycarbonyl group, that is, an alkoxycarbonylamino group include, for example, methoxycarbonylamino, ethoxycarbonylamino, n-propoxycarbonylamino, n-butoxycarbonylamino, tert-butoxycarbonylamino, pentyloxycarbonylamino, hexyloxycarbonylamino, and the like.

Specific examples of the amino group substituted with the aryloxycarbonyl group, that is, an aryloxycarbonylamino group may be, for example, an amino group wherein one hydrogen in an amino group is substituted with the above-mentioned aryloxycarbonyl group. Specific examples thereof include, for example, phenoxycarbonylamino, naphthyloxycarbonylamino, and the like.

Specific examples of the amino group substituted with the aralkyloxycarbonyl group, that is, an aralkyloxycarbonylamino group include, for example, benzyloxycarbonylamino, phenethyloxycarbonylamino, and the like.

Specific examples of the amino group substituted with the substituted sulfonyl group include —$NHSO_2CH_3$, —$NHSO_2C_6H_5$, —$NHSO_2C_6H_4CH_3$, —$NHSO_2CF_3$, —$NHSO_2N(CH_3)_2$, and the like.

Also, a cyclic amino group include, for example, a case where a nitrogen-containing ring is formed by bonding through an alkylene group. The alkylene group may be linear or branched, and include, for example, an alkylene group having 1 to 6 carbon atom(s). Specific examples thereof include, for example, methylene, ethylene, propylene, trimethylene, butylene, 2-methylpropylene, pentylene, 2,2-dimethylpropylene, 2-ethylpropylene, hexylene, and the like. Said alkylene group may have an oxygen atom, a nitrogen atom, a carbonyl group and the like, or a double bond at an arbitrary position of a terminal or a chain in said alkylene group.

Specific examples of the alkylene group having an oxygen atom, a nitrogen atom, a carbonyl group or the like include, for example, —$CH_2CH_2OCH_2CH_2$—, —$CH_2CH_2NHCH_2CH_2$—, and the like.

Specific examples of the cyclic amino group include, for example, piperidino, morpholino, and the like.

The "optionally substituted hydrocarbon group" in the present invention can be defined as a hydrocarbon group having 1 to 20 carbon atom(s), preferably 1 to 15 carbon atom(s), more preferably 1 to 10 carbon atom(s), which is optionally substituted with one or more substituents selected from the group consisting of: an optionally substituted hydrocarbon group having 1 to 20 carbon atom(s), preferably 1 to 15 carbon atom(s), more preferably 1 to 10 carbon atom(s); a halogen atom; a hydrocarbon group which is substituted with one or more halogen atoms, having 1 to 20 carbon atom(s), preferably 1 to 15 carbon atom(s), more preferably 1 to 10 carbon atom(s) (a halogenated hydrocarbon group); an optionally substituted alkoxy group having 1 to 20 carbon atom(s), preferably 1 to 15 carbon atom(s), more preferably 1 to 10 carbon atom(s); an optionally substituted aryloxy group having 6 to 20 carbon atoms, preferably 6 to 15 carbon atoms; an optionally substituted aralkyloxy group having 7 to 20 carbon atoms, preferably 7 to 15 carbon atoms; a substituted amino group which is substituted with one or two substituents selected from the group consisting of an alkyl group having 1 to 20 carbon atom(s), preferably 1 to 15 carbon atom(s), more preferably 1 to 10 carbon atom(s), an aryl group having 6 to 20 carbon atoms, preferably 6 to 15 carbon atoms, an aralkyl group having 7 to 20 carbon atoms, preferably 7 to 15 carbon atoms, an acyl group derived from a carboxylic acid such as an aliphatic carboxylic acid, an aromatic carboxylic acid and the like, having 1 to 20 carbon atom(s), an alkoxycarbonyl group having 1 to 15 carbon atom(s), more preferably 1 to 10 carbon atom(s), an aryloxycarbonyl group having 6 to 20 carbon atoms, preferably 6 to 15 carbon atoms, an aralkyloxycarbonyl group having 7 to 20 carbon atoms, preferably 7 to 15 carbon atoms, a substituted sulfonyl group represented by the formula: $R^a$—$SO_2$— [wherein $R^a$ represents an optionally substituted hydrocarbon group or a substituted amino group] and an alkylene group having 1 to 6 carbon atom(s) and may have an oxygen atom, a nitrogen atom or a carbonyl group in the carbon chain thereof; a nitro group; and a cyano group.

The optionally substituted hydrocarbon group and the substituted amino group represented by $R^{13}$ in —$SO_2R^{13}$ represented by $R^1$ and $R^2$ in the formulae (1) and (2) and other formulae may be the same as described above. This substituted amino group may be the same as described above, and can be defined as a substituted amino group which is substituted with one or two substituents selected from the group consisting of, for example, an alkyl group having 1 to 20 carbon atom(s), preferably 1 to 15 carbon atom(s), more preferably 1 to 10 carbon atom(s), an aryl group having 6 to 20 carbon atoms, preferably 6 to 15 carbon atoms, an aralkyl group having 7 to 20 carbon atoms, preferably 7 to 15 carbon atoms, an acyl group derived from a carboxylic acid such as an aliphatic carboxylic acid, an aromatic carboxylic acid and the like having 1 to 20 carbon atom(s), an alkoxycarbonyl group having 1 to 15 carbon atom(s), more preferably 1 to 10 carbon atom(s), an aryloxycarbonyl group having 6 to 20 carbon atoms, preferably 6 to 15 carbon atoms, an aralkyloxycarbonyl group having 7 to 20 carbon atoms, preferably 7 to 15 carbon atoms, and a substituted sulfonyl group represented by the formula: $R^a$—$SO_2$— [wherein $R^a$ represents an optionally substituted hydrocarbon group, or a substituted amino group], and an alkylene group having 1 to 6 carbon atom(s) and may have an oxygen atom, a nitro group, and a carbonyl group in the carbon chain thereof.

The camphoryl group in the above-mentioned $R^{13}$ is a group wherein one hydrogen atom is removed from camphor. The camphor may be a d-form or l-form, or may be a racemic form.

The optionally substituted hydrocarbon group represented by $R^3$ to $R^{12}$ in the above-mentioned formulae (1) and (2) and other formulae may be the same as the optionally substituted hydrocarbon group described in $R^1$ and $R^2$.

The optionally substituted heterocyclic group may be a heterocyclic group and a substituted heterocyclic group. Examples of the heterocyclic group include an aliphatic heterocyclic group and an aromatic heterocyclic group.

The aliphatic heterocyclic group includes, for example, a 5- to 8-membered, preferably 5- or 6-membered monocyclic, polycyclic or fused-cyclic aliphatic heterocyclic group having 2 to 14 carbon atoms and contains at least one, preferably 1 to 3 heteroatoms such as a nitrogen atom, oxygen atom and/or a sulfur atom. Specific examples of the aliphatic heterocyclic group include, for example, pyrrolidyl-2-one, piperidino, piperadinyl, morpholino, morpholinyl, tetrahydrofuryl, tetrahydropyranyl, and the like.

The aromatic heterocyclic group includes, for example, a 5- to 8-membered, preferably 5- or 6-membered monocyclic, polycyclic or fused-cyclic heteroaryl group having 2 to 15 carbon atoms and contains at least one, preferably 1 to 3 heteroatoms such as a nitrogen atom, oxygen atom and/or a sulfur atom. Specific examples thereof include, for example, furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phtharazyl, quinazolyl, naphthylidyl, cynnolyl, benzoimidazolyl, benzooxazolyl, benzothiazolyl, acridyl, acridinyl, and the like.

The substituted heterocyclic group (the heterocyclic group having a substituent) may be a heterocyclic group wherein at least one hydrogen in the above-mentioned heterocyclic group is substituted with a substituent, that is, a substituted aliphatic heterocyclic group and a substituted aromatic heterocyclic group. The substituent may be the same as the substituent in the optionally substituted hydrocarbon group which has been described in $R^1$ and $R^2$. Accordingly, in the present invention, the "optionally substituted heterocyclic group" can be defined as a 5- to 8-membered, preferably 5- or 6-membered monocyclic, polycyclic or fused-cyclic, saturated or unsaturated heterocyclic group which contains at least one, preferably 1 to 3 heteroatoms such as a nitrogen atom, an oxygen atom or a sulfur atom, and which is optionally substituted with one or more substituents selected from the group consisting of: an optionally substituted hydrocarbon group having 1 to 20 carbon atom(s), preferably 1 to 15 carbon atom(s), more preferably 1 to 10 carbon atom(s); a halogen atom; a hydrocarbon group which is substituted with one or more halogen atoms (a halogenated hydrocarbon group) having 1 to 20 carbon atom(s), preferably 1 to 15 carbon atom(s), more preferably 1 to 10 carbon atom(s); an optionally substituted alkoxy group having 1 to 20 carbon atom(s), preferably 1 to 15 carbon atom(s), more preferably 1 to 10 carbon atom(s); an optionally substituted aryloxy group having 6 to 20 carbon atoms, preferably 6 to 15 carbon atoms; an optionally substituted aralkyloxy group having 7 to 20 carbon atoms, preferably 7 to 15 carbon atoms; a substituted amino group which is substituted with one or two substituents selected from the group consisting of an alkyl group having 1 to 20 carbon atom(s), preferably 1 to 15 carbon atom(s), more preferably 1 to 10 carbon atom(s), an aryl group having 6 to 20 carbon atoms, preferably 6 to 15 carbon atoms, an aralkyl group having 7 to 20 carbon atoms, preferably 7 to 15 carbon atoms, an acyl group derived from a carboxylic acid such as an aliphatic carboxylic acid, an aromatic carboxylic acid and the like, having 1 to 20 carbon atom(s), an alkoxycarbonyl group having 1 to 15 carbon atom(s), more preferably 1 to 10 carbon atom(s), an aryloxycarbonyl group having 6 to 20 carbon atoms, preferably 6 to 15 carbon atoms, an aralkyloxycarbonyl group having 7 to 20 carbon atoms, preferably 7 to 15 carbon atoms, a substituted sulfonyl group represented by the formula: $R^a$—$SO_2$— [wherein $R^a$ represents an optionally substituted hydrocarbon group or a substituted amino group], and an alkylene group having 1 to 6 carbon atom(s) and may have an oxygen atom, a nitrogen atom or a carbonyl group in the carbon chain thereof; a nitro group; and a cyano group.

The optionally substituted alkoxy group, the optionally substituted aryloxy group, and the optionally substituted aralkyloxy group each represented by $R^3$ to $R^{12}$ may be the same as the optionally substituted alkoxy group having 1 to 20 carbon atom(s), preferably 1 to 15 carbon atom(s), more preferably 1 to 10 carbon atom(s), the optionally substituted aryloxy group having 6 to 20, preferably 6 to 15 carbon atoms, and the optionally substituted aralkyloxy group having 7 to 20, preferably 7 to 15 carbon atoms, which have each been described as the substituent in the optionally substituted hydrocarbon group described in $R^1$ and $R^2$. The substituent(s) may be one or more substituents mentioned above selected from the group consisting of: an optionally substituted hydrocarbon group having 1 to 20 carbon atom(s), preferably 1 to 15 carbon atom(s), more preferably 1 to 10 carbon atom(s); halogen atom; a hydrocarbon group substituted with one or more halogen atoms having 1 to 20 carbon atom(s), preferably 1 to 15 carbon atom(s), more preferably 1 to 10 carbon atom(s) (a halogenated hydrocarbon group); an optionally substituted alkoxy group having 1 to 20 carbon atom(s), preferably 1 to 15 carbon atom(s), more preferably 1 to 10 carbon atom(s); an optionally substituted aryloxy group having 6 to 20 carbon atoms, preferably 6 to 15 carbon atoms; an optionally substituted aralkyloxy group having 7 to 20 carbon atoms, preferably 7 to 15 carbon atoms; a substituted amino group which is substituted with one or two substituents selected from the group consisting of an alkyl group having 1 to 20 carbon atom(s), preferably 1 to 15 carbon atom(s), more preferably 1 to 10 carbon atom(s), an aryl group having 6 to 20 carbon atoms, preferably 6 to 15 carbon atoms, an aralkyl group having 7 to 20 carbon atoms, preferably 7 to 15 carbon atoms, an acyl group derived from a carboxylic acid such as an aliphatic carboxylic acid, an aromatic carboxylic acid and the like having 1 to 20 carbon atom(s), an alkoxycarbonyl group having 1 to 15 carbon atom(s), more preferably 1 to 10 carbon atom(s), an aryloxycarbonyl group having 6 to 20 carbon atoms, preferably 6 to 15 carbon atoms, an aralkyloxycarbonyl group having 7 to 20 carbon atoms, preferably 7 to 15 carbon atoms, a substituted sulfonyl group represented by the formula: $R^a$—$SO_2$— (wherein $R^a$ represents an optionally substituted hydrocarbon group or a substituted amino group), and an alkylene group having 1 to 6 carbon atom(s) and may have an oxygen atom, a nitrogen atom or a carbonyl group; a nitro group; and a cyano group in the carbon chain thereof.

The substituted amino group represented by $R^3$ to $R^{12}$ may be the same as or different from the above-mentioned substituted amino group, and may be, for example, a group represented by —$NR^{14}R^{15}$ (wherein $R^{14}$ and $R^{15}$ each independently represent a hydrogen atom, an optionally substituted hydrocarbon group, an optionally substituted heterocyclic group, an optionally substituted acyl group, an optionally substituted alkoxycarbonyl group, an optionally substituted aryloxycarbonyl group, an optionally substituted aralkyloxycarbonyl group, a substituted sulfonyl or the like. Also, $R^{14}$ and $R^{15}$ may be bonded to each other to form a ring, provided that $R^{14}$ and $R^{15}$ are not simultaneously hydrogen atoms).

The optionally substituted alkoxycarbonyl group represented by $R^{14}$ and $R^{15}$ may be an alkoxycarbonyl group and a substituted alkoxycarbonyl group.

The alkoxycarbonyl group may be linear, branched or cyclic, and includes, for example, an alkoxycarbonyl group having 2 to 20 carbon atoms. Specific examples thereof include, for example, methoxycarbonyl, ethoxycarbonyl, n-propoxycarbonyl, 2-propoxycarbonyl, n-butoxycarbonyl, tert-butoxycarbonyl, pentyloxycarbonyl, hexyloxycarbonyl, 2-ethylhexyloxycarbonyl, lauryloxycarbonyl, stearyloxycarbonyl, cyclohexyloxycarbonyl, and the like.

The substituted alkoxycarbonyl group (the alkoxycarbonyl group having a substituent) may be an alkoxycarbonyl group wherein at least one hydrogen atom in the above-mentioned alkoxycarbonyl group is substituted with a substituent. The substituent may be the same as the substituent in the optionally substituted hydrocarbon group described in $R^1$ and $R^2$.

Specific examples of the substituted alkoxycarbonyl group include, for example, 2,2,2-trichloroethoxycarbonyl, 1,1-dimethyl-2,2,2-trichloroethoxycarbonyl, and the like.

The optionally substituted aryloxycarbonyl group may be an aryloxycarbonyl group and a substituted aryloxycarbonyl group.

The aryloxycarbonyl group includes, for example, an aryloxycarbonyl group having 7 to 20 carbon atoms. Specific examples thereof include, for example, phenoxycarbonyl, naphthyloxycarbonyl, and the like.

The substituted aryloxycarbonyl group (the aryloxycarbonyl group having a substituent) may be an aryloxycarbonyl group wherein at least one hydrogen atom in the above-mentioned aryloxycarbonyl group is substituted with a substituent. The substituent may be the same as the substituent in the optionally substituted hydrocarbon group described in $R^1$ and $R^2$.

The optionally substituted aralkyloxycarbonyl group may be an aralkyloxycarbonyl group and a substituted aralkyloxycarbonyl group.

The aralkyloxycarbonyl group includes, for example, an aralkyloxycarbonyl group having 8 to 20 carbon atoms. Specific examples thereof include, for example, benzyloxycarbonyl, phenylethoxycarbonyl, 9-fluorenylmethyloxycarbonyl groups, and the like.

The substituted aralkyloxycarbonyl group (the aralkyloxycarbonyl group having a substituent) may be an aralkyloxycarbonyl group wherein at least one hydrogen atom in the above-mentioned aralkyloxycarbonyl group is substituted with a substituent. The substituent may be the same as the substituent in the optionally substituted hydrocarbon group described in $R^1$ and $R^2$.

Specific examples of the substituted aralkyloxycarbonyl group include, for example, 4-nitrobenzyloxycarbonyl, 4-methoxybenzyloxycarbonyl, 4-methylbenzyloxycarbonyl, 3,4-dimethoxybenzyloxycarbonyl, and the like.

Specific examples of the substituted amino group include an amino group substituted with the alkyl group, an amino group substituted with the aryl group, an amino group substituted with the aralkyl group, an amino group substituted with the acyl group, an amino group substituted with the alkoxycarbonyl group, an amino group substituted with the aryloxycarbonyl group, an amino group substituted with the aralkyloxycarbonyl group, and an amino group substituted with the substituted sulfonyl group, and the like.

Specific examples of the amino group substituted with the alkyl group, that is, the alkyl-substituted amino group include, for example, mono- or di-alkylamino groups such as N-methylamino, N,N-dimethylamino, N,N-diethylamino, N,N-diisopropylamino, N-cyclohexylamino, and the like.

Specific examples of the amino group substituted with the aryl group, that is, the aryl-substituted amino group include, for example, mono- or di-arylamino groups such as N-phenylamino, N,N-diphenylamino, N-naphthylamino, N-naphthyl-N-phenylamino, and the like.

Specific examples of the amino group substituted with the aralkyl group, that is, the aralkyl-substituted amino group include, for example, mono- or di-aralkylamino groups such as N-benzylamino, N,N-dibenzylamino, and the like.

Specific examples of the amino group substituted with the acyl group, that is, the acylamino group include, for example, formylamino, acetylamino, propionylamino, pivaloylamino, pentanoylamino, hexanoylamino, benzoylamino, and the like.

Specific examples of the amino group substituted with the alkoxycarbonyl group, that is, the alkoxycarbonylamino group include, for example, methoxycarbonylamino, ethoxycarbonylamino, n-propoxycarbonylamino, n-butoxycarbonylamino, tert-butoxycarbonylamino, pentyloxycarbonylamino, hexyloxycarbonylamino, and the like.

A specific example of the amino group substituted with the aryloxycarbonyl group, that is, the aryloxycarbonylamino group include, for example, an amino group wherein one hydrogen atom in an amino group is substituted with the above-mentioned aryloxycarbonyl group. Specific examples thereof include, for example, phenoxycarbonylamino, naphthyloxycarbonylamino, and the like.

Specific examples of the amino group substituted with the aralkyloxycarbonyl group, that is, the aralkyloxycarbonylamino group include, for example, benzyloxycarbonylamino, and the like.

Specific examples of the amino group substituted with the substituted sulfonyl group include, for example, $-NHSO_2CH_3$, $-NHSO_2C_6H_5$, $-NHSO_2C_6H_4CH_3$, $-NHSO_2CF_3$, $-NHSO_2N(CH_3)_2$, and the like.

Also, the case that $R^{14}$ and $R^{15}$ are bonded to each other to form a ring includes, for example, a case where a nitrogen-containing ring is formed by bonding through an alkylene group. The alkylene group may be linear or branched, and includes, for example, an alkylene group having 1 to 6 carbon atom(s). Specific examples thereof include, for example, methylene, ethylene, propylene, trimethylene, butylene, 2-methylpropylene, pentylene, 2,2-dimethylpropylene, 2-ethylpropylene, hexylene, and the like. Also, said alkylene group may have an oxygen atom, a nitrogen atom, a carbonyl group and the like, or a double bond at a an arbitrary position of a terminal or a chain in said alkylene group.

Specific examples of the alkylene group having an oxygen atom, a nitrogen atom, a carbonyl group and the like include, for example, $-CH_2CH_2OCH_2CH_2-$, $-CH_2CH_2NHCH_2CH_2-$, and the like.

Specific examples of the substituted amino group in the case that $R^{14}$ and $R^{15}$ are bonded to each to form a ring include, for example, piperidino, morpholino, and the like.

In the above-mentioned formulae (1) and (2) and other formulae, it is indispensable that at least one of $R^3$ to $R^7$ and $R^8$ to $R^{12}$ is the substituted amino group. It is more preferred that in each of $R^3$ to $R^7$ and $R^8$ to $R^{12}$ respectively, at least one thereof is the substituted amino group.

In the above-mentioned formulae (2) and (3) and other formulae, the transition metal represented by M includes, for example, a transition metal in the groups VIII to X in the periodic table of elements, preferably a transition metal in the groups VIII to IX in the periodic table of elements. Preferred specific examples thereof include, for example, ruthenium, rhodium, iridium, and the like.

The halogen atom represented by X includes fluorine, chlorine, bromine, iodine, and the like, preferably chlorine, bromine and iodine, and so on.

The ligand represented by L is preferably a neutral ligand. The neutral ligand includes an aromatic compound which may be substituted with an alkyl group, an olefin compound, other neutral ligands, and the like.

The aromatic compound which may be substituted with an alkyl group may be an unsubstituted aromatic compound and an alkyl-substituted aromatic compound.

The unsubstituted aromatic compound includes benzene, and the like.

The alkyl-substituted aromatic compound includes, for example, an aromatic compound wherein at least one hydrogen atom in the above-mentioned aromatic compound is substituted with an alkyl group having 1 to 3 carbon atom(s), such as methyl, ethyl, propyl and isopropyl. Specific examples thereof include, for example, toluene, p-cymene, hexamethylbenzene, 1,3,5-trimethylbenzene (mesitylene), and the like.

The olefin compound includes, for example, ethylene, cyclopentadiene, 1,5-cyclooctadiene (cod), norbornadiene (nbd), pentamethylcyclopentadiene, and the like.

The other neutral ligand includes N,N-dimethylformamide (DMF), acetonitrile, benzonitrile, acetone, chloroform, and the like.

The optically active diamine compound represented by the formula (1) of the present invention [hereinafter abbreviated to the optically active diamine compound (1)] includes (1R, 2R), (1S,2S), (1R,2S) and (1S,2R) forms. Among these, (1R, 2R) and (1S,2S) forms are preferred.

Specific examples of the above-mentioned optically active diamine compound (1) include, for example, (1R,2R)-1,2-di(4-N,N-dimethylaminophenyl)ethylenediamine, (1S,2S)-1,2-di(4-N,N-dimethylaminophenyl)ethylenediamine, (1R,2R)-1,2-di(4-N,N-diethylaminophenyl)ethylenediamine, (1S,2S)-1,2-di(4-N,N-diethylaminophenyl)ethylenediamine, (1R,2R)-1,2-di(4-N,N-dipropylaminophenyl)ethylenediamine, (1S,2S)-1,2-di(4-N,N-dipropylaminophenyl)ethylenediamine, and optically active substances of the diamine compounds represented by the formula (1b), which will be illustrated below.

All of the diamine compounds represented by the formula (1b) are novel compounds including racemic form thereof. Among these, said diamine compounds which are optically active are preferred examples of the above-mentioned optically active diamine compound (1), and are highly useful.

Among the amine compounds represented by the formula (1b), specific examples of the optically active diamine compounds include, for example, (1R,2R)-(N-benzenesulfonyl)-1,2-di(4-N,N-dimethylaminophenyl)ethylenediamine, (1S,2S)-(N-benzenesulfonyl)-1,2-di(4-N,N-dimethylaminophenyl)ethylenediamine, (1R,2R)-(N-p-toluenesulfonyl)-1,2-di(4-N,N-dimethylaminophenyl)ethylenediamine, (1S,2S)-(N-p-toluenesulfonyl)-1,2-di(4-N,N-dimethylaminophenyl)ethylenediamine, (1R,2R)-(N-methanesulfonyl)-1,2-di(4-N,N-dimethylaminophenyl)ethylenediamine, (1S,2S)-(N-methanesulfonyl)-1,2-di(4-N,N-dimethylaminophenyl)ethylenediamine, (1R,2R)-(N-trifluoromethansulfonyl)-1,2-di(4-N,N-dimethylaminophenyl)ethylenediamine, (1S,2S)-(N-trifluoromethansulfonyl)-1,2-di(4-N,N-dimethylaminophenyl)ethylenediamine, (1R,2R)-(N-benzenesulfonyl)-1,2-di(4-N,N-diethylaminophenyl)ethylenediamine, (1S,2S)-(N-benzenesulfonyl)-1,2-di(4-N,N-diethylaminophenyl)ethylenediamine, (1R,2R)-(N-benzenesulfonyl)-1,2-di(4-N,N-dipropylaminophenyl)ethylenediamine, (1S,2S)-(N-benzenesulfonyl)-1,2-di(4-N,N-dipropylaminophenyl)ethylenediamine, and the like.

Other preferred examples of the optically active diamine compound (1) are the optically active diamine compound represented by the following formula (1a):

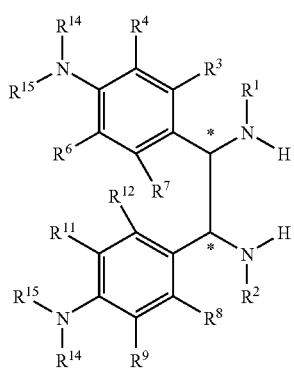

(1a)

wherein $R^1$ to $R^4$, $R^6$ to $R^9$, $R^{11}$, $R^{12}$, $R^{14}$, $R^{15}$ and * are the same as described above.

Also, among the diamine compounds represented by the formula (1b), preferred examples of the optically active diamine compound (which is also the preferred examples of the optically active diamine compound (1)) include the optically active diamine compound represented by the following formula (1c):

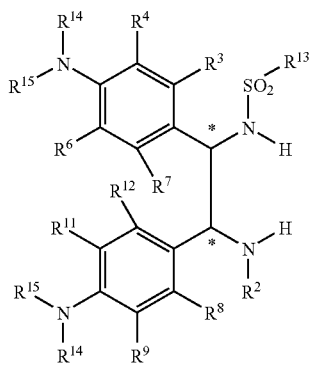

(1c)

wherein $R^2$ to $R^4$, $R^6$ to $R^9$, $R^{11}$ to $R^{15}$ and * are the same as described above.

The optically active transition metal-diamine complex represented by the formula (2) of the present invention [hereinafter abbreviated to the optically active transition metal-diamine complex (2)] includes (1R,2R), (1S,2S), (1R,2S) and (1S,2R) forms. Among these, (1R,2R) and (1S,2S) forms are preferred.

Specific examples of the optically active transition metal-diamine complex (2) include, for example, the following compounds:

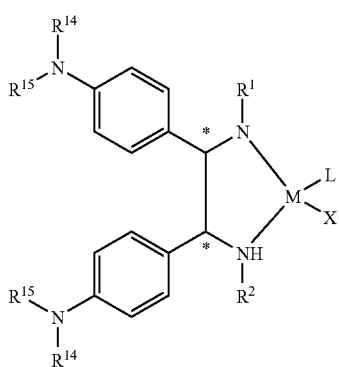

(1)

-continued

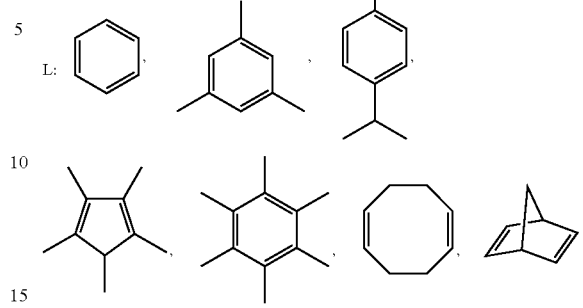

$R^1, R^2$:H, —SO$_2$C$_6$H$_5$, —SO$_2$C$_6$H$_4$-p-CH$_3$, —SO$_2$C$_6$H$_4$-p-SO$_3$Na,
—SO$_2$CF$_3$, —SO$_2$-thienyl $R^{14}, R^{15}$:CH$_3$, C$_2$H$_5$, C$_3$H$_7$
M:Ru, Rh, Ir
X:Cl, Br, I Preferred examples of the optically active transition metal-diamine complex represented by the formula (2) of the present invention include the optically active transition metal-diamine complex represented by the following formula (2a):

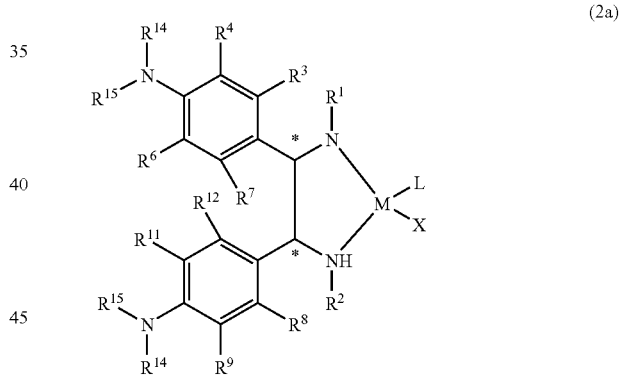

(2a)

wherein $R^1$ to $R^4$, $R^6$ to $R^9$, $R^{11}$, $R^{12}$, $R^{14}$, $R^{15}$, M, X, L and * are the same as described above.

The optically active diamine compound represented by the formula (1) of the present invention and the optically active transition metal-diamine complex represented by the formula (2) may each be an acid salt thereof if necessary. That is, the optically active diamine compound represented by the formula (1) and the optically active transition metal-diamine complex represented by the formula (2) include acid salts thereof in the scope of the present invention. Further, each of the compound and the complex which does not form any acid salt but is substantially in the form of an acid salt is also included therein.

The acid salt of the optically active diamine compound represented by the above-mentioned formula (1) include an acid salt represented by the formula (1d):

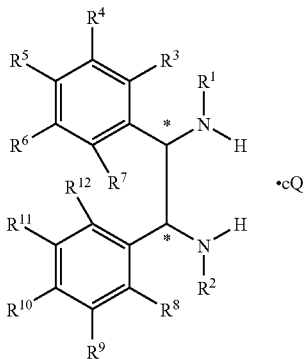

(1d)

wherein Q represents an acid, c represents a natural number, and $R^1$ to $R^{12}$ and * are the same as described above.

The acid salt of the optically active transition metal-diamine complex represented by the above-mentioned formula (2) include, for example, an acid salt represented by the formula (2c):

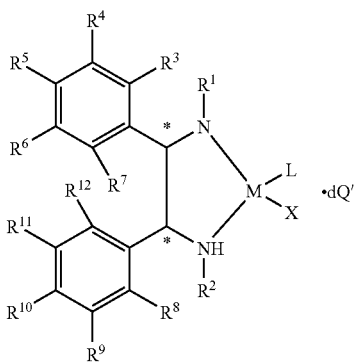

(2c)

wherein Q' represents an acid, d represents a natural number, and $R^1$ to $R^{12}$, X, L and * are the same as described above.

The acid represented by Q and Q' in the above-mentioned formulae (1d) and (2c) are not particularly limited if the acid can form the acid salt or substantially form acid salt to the optically active diamine compound represented by the above-mentioned formula (1) and the optically active transition metal-diamine complex represented by the above-mentioned formula (2), respectively. The acid include an inorganic acid, an organic acid, a Lewis acid and the like. The inorganic acid includes, for example, hydrochloric acid, hydrobromic acid, sulfuric acid, phosphoric acid, tetrafluoroboric acid, perchloric acid, periodic acid, and the like. The organic acid includes, for example, carboxylic acids such as formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, and glycolic acid; sulfonic acids such as methansulfonic acid, benzenesulfonic acid, p-toluenesulfonic acid, and trifluoromethanesulfonic acid; and the like. The Lewis acid includes, for example, aluminum halides such as aluminum chloride, and aluminum bromide; dialkylaluminum halides such as diethylaluminum chloride, diethylaluminum bromide, diisopropylaluminum chloride; trialkoxyaluminums such as triethoxyaluminum, triisopropoxyaluminum, and tri-tert-butoxyaluminum; titanium halides such as titanium tetrachloride; tetraalkoxytitaniums such as tetraisopropoxytitanium; boron halides such as boron trifluoride, boron trichloride, boron tribromide, and a boron trifluoride/diethyl ether complex; zinc halides such as zinc chloride, and zinc bromide; and the like.

These acids may be used alone or in combination of two or more thereof. The acid salt of the above-mentioned formulae (1d) or (2c) may be made only of one acid salt, or may be a mixture of acid salts of two or more different acids (that is, a mixture of acid salts).

The natural numbers represented by c and d are each at least 1, and are varied in accordance with the structure of the above-mentioned optically active diamine compound and the optically active transition metal-diamine complex, respectively, on the basis of the number of the substituted amino groups substituted in (bonded to) $R^3$ to $R^{12}$. The natural numbers are each appropriately selected from the range of 1 or more, preferably 1 to 12, more preferably 2 to 4.

These acid salts can be produced by a usual method.

Specific examples of the transition metal compound represented by the above-mentioned formula (3) used in the present invention [hereinafter abbreviated to the transition metal compound (3)] include, for example, [RuCl$_2$(benzene)]$_2$, [RuBr$_2$(benzene)]$_2$, [RuI$_2$(benzene)]$_2$, [RuCl$_2$(p-cymene)]$_2$, [RuBr$_2$(p-cymene)]$_2$, [RuI$_2$(p-cymene)]$_2$, RuCl$_2$(hexamethylbenzene)]$_2$, [RuBr$_2$(hexamethylbenzene)]$_2$, [RuI$_2$(hexamethylbenzene)]$_2$, [RuCl$_2$(mesitylene)]$_2$, [RuBr$_2$(mesitylene)]$_2$, [RuI$_2$(mesitylene)]$_2$, [RuCl$_2$(pentamethylcyclopentadiene)]$_2$, [RuBr$_2$(pentamethylcyclopentadiene)]$_2$, [RuI$_2$(pentamethylcyclopentadiene)]$_2$, [RuCl$_2$(cod)]n, [RuBr$_2$(cod)]n, [RuI$_2$(cod)]n, [RuCl$_2$(nbd)]n, [RuBr$_2$(nbd)]n, [RuI$_2$(nbd)]n, RuCl$_3$ hydrate, RuBr$_3$ hydrate, RuI$_3$ hydrate, [RhCl$_2$(cyclopentadiene)]$_2$, [RhBr$_2$(cyclopentadiene)]$_2$, [RhI$_2$(cyclopentadiene)]$_2$, [RhCl$_2$(pentamethylcyclopentadiene)]$_2$, [RhBr2(pentamethylcyclopentadiene)]$_2$, [RhI$_2$(pentamethylcyclopentadiene)]$_2$, [RhCl(cod)]$_2$, [RhBr(cod)]$_2$, [RhI(cod)]$_2$, [RhCl(nbd)]$_2$, [RhBr(nbd)]$_2$, [RhI(nbd)]$_2$, RhCl$_3$ hydrate, RhBr$_3$ hydrate, RhI$_3$ hydrate, [IrCl$_2$(cyclopentadiene)]$_2$, [IrBr$_2$(cyclopentadiene)]$_2$, [IrI$_2$(cyclopentadiene)]$_2$, [IrCl$_2$(pentamethylcyclopentadiene)]$_2$, [IrBr$_2$(pentamethylcyclopentadiene)]$_2$, [IrI$_2$(pentamethylcyclopentadiene)]$_2$, [IrCl(cod)]$_2$, [IrBr(cod)]$_2$, [IrI(cod)]$_2$, [IrCl(nbd)]$_2$, [IrBr(nbd)]$_2$, [IrI(nbd)]$_2$, IrCl$_3$ hydrate, IrBr$_3$ hydrate, IrI$_3$ hydrate, and the like, provided that in the above-mentioned formulae, n represents a positive number, cod represents 1,5-cyclooctadiene, and nbd represents norbornadiene.

The optically active diamine compound (1) of the present invention can be produced, for example, as follows:

(1) Production of a Dibenzoazine

For example, a benzaldehyde represented by the formula (6):

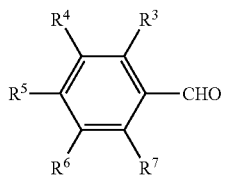

(6)

wherein $R^3$ to $R^7$ are the same as described above; is reacted with a hydrazine salt optionally in water and/or an appropriate organic solvent to give a dibenzoazine represented by the formula (7):

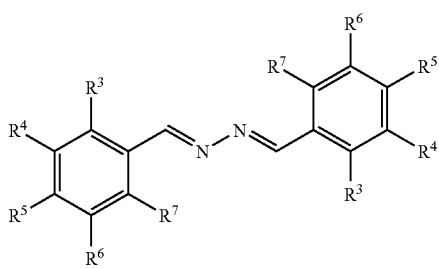

(7)

wherein $R^3$ to $R^7$ are the same as described above.

The hydrazine salt includes, for example, hydrazine sulfate, hydrazine hydrochloride, hydrazine acetate, and the like.

The amount of the hydrazine salt used is appropriately selected usually from the range of 0.3 to 0.5, preferably 0.35 to 0.45 to the benzaldehyde represented by the formula (6).

Water is used to dissolve the hydrazine salt. The amount of water used is appropriately selected from the range of 2 to 10 times, more preferably 3 to 5 times to the hydrazine salt.

The organic solvent other than water may be used, if necessary, and the examples thereof include, for example, ethers such as diethyl ether, diisopropyl ether, tert-butyl methyl ether, dimethoxyethane, ethylene glycol diethyl ether, tetrahydrofuran, 1,4-dioxane and 1,3-dioxolane; alcohols such as methanol, ethanol, 2-propanol, n-butanol, 2-ethoxyethanol and benzyl alcohol; esters such as methyl acetate, ethyl acetate, n-butyl acetate and methyl propionate; amides such as formamide, N,N-dimethylformamide and N,N-dimethylacetoamide; cyano-containing organic compounds such as acetonitrile; N-methylpyrrolidone; and the like. These solvents may be used alone or in an appropriate combination of two or more thereof.

The amount of the organic solvent used other than water is appropriately selected usually from the range of 2 to 10 times, preferably 3 to 5 times to the aldehyde.

The above-mentioned reaction is conducted in the presence of a base if necessary. The base includes an inorganic base, an organic base, and the like.

The inorganic base include alkali metal hydroxides such as lithium hydroxide, sodium hydroxide and potassium hydroxide; metal carbonates such as sodium carbonate, potassium carbonate, magnesium carbonate and calcium carbonate; metal hydrogencarbonates such as sodium hydrogencarbonate and potassium hydrogencarbonate; metal hydrides such as sodium hydride, sodium borohydride and lithium aluminum hydride; ammonium gas; ammonia water; and the like. In the case of ammonia water, the preferred concentration thereof is usually 10 to 40% although the concentration thereof is not particularly limited.

The organic base include alkali metal alkoxides such as potassium methoxide, sodium methoxide, lithium methoxide, sodium ethoxide, potassium isopropoxide and potassium tert-butoxide; potassium naphthalenide; organic acid salts of an alkali-alkaline earth metal such as sodium acetate, potassium acetate, magnesium acetate and calcium acetate; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine; organic metal compounds such as methylmagnesium bromide, ethylmagnesium bromide, propylmagnesium bromide, methyllithium, ethyllithium, propyllithium, n-butyllithium and tert-butyllithium; quaternary ammonium salts; and the like.

The amount of base used in the case of, for example, 28% ammonia water is appropriately selected from the range of 1.5 to 2.5 equivalents, more preferably 1.7 to 2.2 equivalents to the amount of the hydrazine salt used.

The reaction temperature is appropriately selected usually from the range of 10 to 50° C., preferably 20 to 40° C.

The reaction time is appropriately selected usually from the range of 1 to 10 hours, preferably 2 to 6 hours.

After the end of the reaction, post-treatment, purification and the like is conducted if necessary. A specific method for the post-treatment include separation and purification methods which are publicly known such as solvent extraction, liquid property conversion, solvent conversion, salting-out, crystallization, recrystallization, various chromatographies.

(2) Production of the Optically Active Diamine Compound (1)

Next, the dibenzoazine represented by the formula (7), which is obtained as described above, is subjected to rearrangement reaction in an appropriate solvent, if necessary, and under inert gas atmosphere, if necessary. After the end of the reaction, post-treatment, purification and the like is conducted, if necessary. A specific method for the post-treatment is the same as described above.

After the post-treatment and the like is conducted if necessary, an optically active substance is separated by a known separation method such as various chromatographies and the like, whereby the optically active diamine compound (1) can be obtained.

The rearrangement reaction is pinacol rearrangement, and is preferably conducted in the presence of zinc and titanium tetrachloride.

The amount of zinc used is appropriately selected usually from the range of 10 equivalents or more, preferably 10 to 15 equivalents to the dibenzoazine.

The amount of titanium tetrachloride used is appropriately selected usually from the range of 5 to 10 equivalents, preferably 5 to 8 equivalents to the dibenzoazine.

The solvent used, if necessary, include, for example, aliphatic hydrocarbons such as pentane, hexane, heptane, octane, decane and cyclohexane; aromatic hydrocarbons such as benzene, toluene and xylene; halogenated hydrocarbons such as dichloromethane, 1,2-dichloroethane, chloroform, carbon tetrachloride and o-dichlorobenzene; ethers such as diethyl ether, diisopropyl ether, tert-butyl methyl ether, dimethoxyethane, ethylene glycol diethyl ether, tetrahydrofuran, 1,4-dioxane and 1,3-dioxolane; esters such as methyl acetate, ethyl acetate, n-butyl acetate and methyl propionate; amides such as formamide, N,N-dimethylformamide and N,N-dimethylacetoamide; sulfoxides such as dimethylsulfoxide; cyano-containing organic compounds such as acetonitrile; N-methylpyrrolidone; water; and the like. These solvents may be used alone or in an appropriate combination of two or more thereof.

The amount of the solvent used is appropriately selected usually from the range of 5 to 20 times, preferably 5 to 10 times the volume to the dibenzoazine.

The rearrangement reaction is preferably conducted under inert gas atmosphere. Examples of the inert gas include nitrogen gas, argon gas, and the like.

The reaction temperature is appropriately selected usually from the range of −60 to 40° C., preferably −40 to 30° C.

The reaction time is appropriately selected usually from the range of 5 to 24 hours, preferably 10 to 24 hours.

(3) Introduction of a Substituted Sulfonyl Group into the N-Position

The introduction of a substituted sulfonyl group into the N-position can be conducted by a publicly known method.

First, a compound wherein a substituted sulfonyl group is to be introduced into the N-position, for example, the optically active diamine compound (1) is reacted with a sulfonylation agent in the presence of a base, if necessary, and in an appropriate solvent to give an optically active N-mono(substituted sulfonyl)-diphenylethylenediamine [an optically active diamine compound wherein either one of $R^1$ or $R^2$ in the formula (1) is —$SO_2R^{13}$ (wherein $R^{13}$ is the same as described above)] or an optically active N-di(substituted sulfonyl)-diphenylethylenediamine [an optically active diamine compound wherein both of $R^1$ and $R^2$ in the formula (1) are —$SO_2R^{13}$ (wherein $R^{13}$ is the same as described above)].

The sulfonylation agent include, for example, a sulfonyl halide represented by the formula (8):

$$R^{13}—SO_2—X^1 \quad (8)$$

wherein $X^1$ represents a halogen atom and $R^{13}$ is the same as described above.

In the formula (8), the halogen atom represented by $X^1$ include fluorine, chlorine, bromine, iodine atoms, and the like.

Specific examples of the sulfonyl halide represented by the formula (8) include, for example, methanesulfonyl chloride, ethanesulfonyl chloride, benzenesulfonyl chloride, p-toluenesulfonyl chloride, trifluoromethanesulfonyl chloride, 2,4,6-mesitylsulfonyl chloride, 2,4,6-triisopropylbenzenesulfonyl chloride, 4-methoxybenzenesulfonyl chloride, 4-chlorobenzenesulfonyl chloride, and the like.

The amount of the sulfonylation agent used is appropriately selected usually from the range of 0.8 to 5 moles, preferably 1 to 2 moles, more preferably 1 to 1.2 moles per 1 mole of the optically active diamine compound (1).

The base used in the reaction includes an inorganic base, an organic base, and the like.

The inorganic base include, for example, salts and hydroxides of an alkali or alkaline earth metal such as potassium carbonate, potassium hydroxide, lithium hydroxide, sodium hydrogencarbonate, sodium carbonate, potassium hydrogencarbonate, sodium hydroxide, magnesium carbonate and calcium carbonate; metal hydrides such as sodium hydride, sodium borohydride, and lithium aluminum hydride; and the like.

The organic base include alkali metal alkoxides such as potassium methoxide, sodium methoxide, lithium methoxide, sodium ethoxide, potassium isopropoxide and potassium tert-butoxide; potassium naphthalenide; organic acid salts of an alkali-alkaline earth metal such as sodium acetate, potassium acetate, magnesium acetate and calcium acetate; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine; organic metal compounds such as methylmagnesium bromide, ethylmagnesium bromide, propylmagnesium bromide, methyllithium, ethyllithium, propyllithium, n-butyllithium and tert-butyllithium; quaternary ammonium salts; and the like.

In the present reaction, organic amines are particularly preferred among these bases.

The amount of the base used is appropriately selected usually from the range of 1.0 to 2.0 equivalents, preferably 1.1 to 1.2 equivalents to the optically active diamine compound (1).

The solvent used in the reaction include, for example, aliphatic hydrocarbons such as pentane, hexane, heptane, octane, decane and cyclohexane; aromatic hydrocarbons such as benzene, toluene and xylene; halogenated hydrocarbons such as dichloromethane, 1,2-dichloroethane, chloroform, carbon tetrachloride and o-dichlorobenzene; ethers such as diethyl ether, diisopropyl ether, tert-butyl methyl ether, dimethoxyethane, ethylene glycol diethyl ether, tetrahydrofuran, 1,4-dioxane and 1,3-dioxolane; ketones such as acetone, methyl ethyl ketone, methyl isobutyl ketone and cyclohexanone; esters such as methyl acetate, ethyl acetate, n-butyl acetate and methyl propionate; amides such as formamide, N,N-dimethylformamide and N,N-dimethylacetoamide; sulfoxides such as dimethylsulfoxide; cyano-containing organic compounds such as acetonitrile; N-methylpyrrolidone; water; and the like. These solvents may be used alone or in an appropriate combination of two or more thereof.

The amount of the solvent used is appropriately selected usually from the range of 2 to 10 times, preferably 5 to 10 times the volume to the optically active diamine compound (1).

The reaction temperature is appropriately selected usually from the range of −10 to 50° C., preferably 0 to 20° C.

The reaction time is appropriately selected usually from the range of 3 to 20 hours, preferably 5 to 10 hours.

After the reaction, the resultant optically active N-monoor di(substituted sulfonyl)-diphenylethylenediamine is arbitrarily subjected to post-treatment, purification or the like, if necessary. A specific method for the post-treatment include separation and purification methods which are publicly known such as solvent extraction, liquid property conversion, solvent conversion, salting-out, crystallization, recrystallization, various chromatographies.

Thus obtained optically active diamine compound (1) is useful as a ligand of an optically active transition metal-diamine complex used as a catalyst for asymmetric synthesis, or as an optical resolution agent, and the like.

The optically active transition metal-diamine complex (2) of the present invention can easily be produced by a method described in Angewandt Chemie Int. Ed. Engl., 36, No. 3, 286 (1997) or other documents. The description in Angewandt Chemie Int. Ed. Engl., 36, No. 3, 286 (1997) is incorporated into the present specification by reference thereto.

That is, for example, the complex can be obtained by causing the optically active diamine compound (1) to react with the transition metal compound (3) according to a usual manner.

Also, in the formula (3), in the case of using the transition metal compound (3) wherein n is 0, the complex can be obtained by causing the optically active diamine compound to react with the transition metal compound and a neutral ligand according to a usual manner. The transition metal compound wherein n is 0 in the formula (3) may be a hydrate.

The amount of the transition metal compound (3) used is appropriately selected usually from the range of 0.1 to 1.0 equivalent, preferably 0.2 to 0.5 equivalents to the optically active diamine compound (1).

The production of the optically active transition metal-diamine complex (2) is preferably conducted in the presence of a solvent. The solvent include, for example, aromatic hydrocarbons such as benzene, toluene, and xylene; halogenated hydrocarbons such as dichloromethane, 1,2-dichloroethane, chloroform, carbon tetrachloride, and o-dichlorobenzene; alcohols such as methanol, ethanol, 2-propanol, n-butanol, 2-ethoxyethanol, and benzyl alcohol; and the like. These solvents may be used alone or in an appropriate combination of two or more thereof.

The amount of the solvent used is appropriately selected usually from the range of 10 to 40 times, preferably 10 to 20 times the volume to the optically active diamine compound (1).

The production of the optically active transition metal-diamine complex (2) can be conducted in the presence of a base, if necessary. The base is preferably an organic base, and specific examples thereof include organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, tetramethylethylenediamine, and N-methylmorpholine; alkoxides of an alkali or alkaline earth metal such as potassium methoxide, sodium methoxide, lithium methoxide, sodium ethoxide, potassium isoproixde, potassium tert-butoxide, lithium methoxide, and potassium naphthalenide; and the like.

The amount of the base used is appropriate selected usually from the range of 0.5 to 5 equivalents, preferably 1 to 3 equivalents to the optically active diamine compound (1).

The reaction temperature varies in accordance with the kinds of the optically active diamine compound (1), the transition metal compound (3) or the like, and others, and is not particularly limited. The temperature is appropriately selected usually from the range of 0 to 100° C., preferably 20 to 80° C.

The reaction time varies spontaneously in accordance with the reaction temperature, the kinds and the amount of the optically active diamine compound (1), the transition metal compound (3), and others used, and is not particularly limited. The time is appropriately selected usually from the range of 1 to 24 hours, preferably 1 to 8 hours.

Thus obtained optically active transition metal-diamine complex (2) of the present invention is characterized by having, as a ligand, an optically active diamine complex having phenyl group(s) which has the substituted amino group, therefore making the optically active transition metal-diamine complex of the present invention water-soluble. As the result, the complex has a high utility value as a catalyst for organic synthesis reaction, and the like. The complex is useful as, for example, a catalyst for asymmetric synthesis, in particular, a catalyst for asymmetric reduction. The asymmetric reduction in the present invention includes reductions such as hydrogenaton wherein molecular hydrogen (that is, hydrogen gas, this matter being also applied to the following description) is preferably used (i.e. catalytic reduction) and reduction based on transfer hydrogenation by a hydrogen atom dereived from a hydrogen donator. In the present specification, catalysts in these reactions are called a catalyst for hydrogenation and a catalyst for transfer hydrogenation, respectively, and catalysts of reduction which include thereof are collectively called a catalyst for reduction.

In the case, for example, where the optically active transition metal-diamine complex (2) of the present invention is used as an catalyst for asymmetric reduction, said optically active transition metal-diamine complex exists in the form of an optically active transition metal-diamine-hydride complex represented by the following formula (2-1) in asymmetric hydrogenation. After the asymmetric hydrogenation, also, said water-soluble transition metal-diamine complex exists in the form of an optically active transition metal-amide complex represented by a the following formula (2-2). The optically active transition metal-diamine-hydride complex and the optically active transition metal-amide complex are also included in the scope of the optically active transition metal-diamine complex of the present invention.

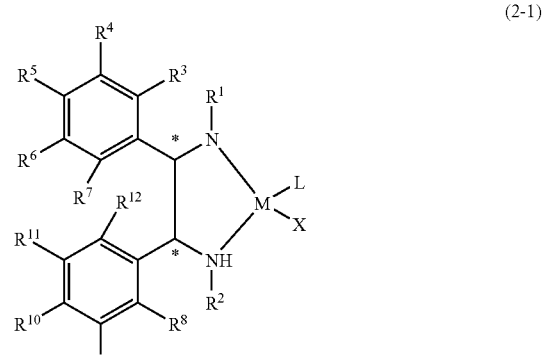

(2-1)

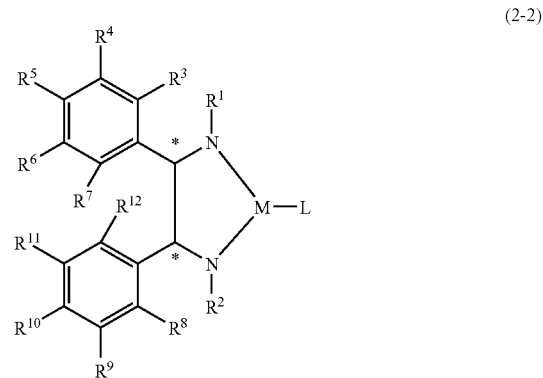

(2-2)

wherein the above-mentioned formulae, $R^1$ to $R^{12}$, M, L and * are the same as described above.

The following will describe a process for producing an alcohol using the optically active transition metal-diamine complex of the present invention as a catalyst for asymmetric reduction. The process for producing an alcohol of the present invention is characterized in that the above-mentioned optically active transition metal-diamine complex of the present invention is used as a catalyst, and it is a process of reducing a carbonyl group of a ketone in the presence of molecular hydrogen or a hydrogen donator, thereby converting the ketone into the corresponding alcohol. In this case, the present invention is further characterized in that, an optically active alcohol can be produced when a prochiral ketone is used as the ketone of the raw material in this case. As the optical activity in the present invention, an optical purity does not necessarily have to be 100%, and is sufficient as long as one of optically active substances is present in a larger than the other of the optically active substances and the optical purity of 50% or more, preferably 70% or more, more preferably 80% or more.

The ketone of the raw material used in the process for producing an alcohol of the present invention includes various carbonyl compounds having a carbonyl group. In the case that such a ketone has functional groups undesired for the reduction thereof, the ketone can be used in the reaction in the state that these undesired functional groups are protected by known various methods. The preferred ketone used in the process of the present invention includes, for example, a ketone represented by the following formula (4):

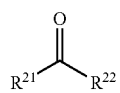

(4)

wherein $R^{21}$ and $R^{22}$ each independently represent an optionally substituted hydrocarbon group, an optionally substituted heterocyclic group, or a ferrocenyl group, provided that $R^{21} \neq R^{22}$, and $R^{21}$ and $R^{22}$ may be bonded to each other to form a cyclic ketone having a substituent.

According to this process of the present invention, an alcohol corresponding to the ketone of the raw material can be produced. In the case of using, for example, the ketone represented by the above-mentioned formula (4) as the ketone of the raw material, an optically active alcohol represented by the following formula (5):

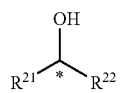

(5)

wherein * represents an asymmetric carbon atom, and $R^{21}$ and $R^{22}$ are the same as described above, can be produced.

In the formulae (4) and (5), the optionally substituted hydrocarbon group represented by $R^{21}$ and $R^{22}$ represents a hydrocarbon group and a substituted hydrocarbon group. The optionally substituted heterocyclic group represents a heterocyclic group and a substituted heterocyclic group. The hydrocarbon group and the heterocyclic group are same as the respective groups described in the above-mentioned formula (1).

The substituted hydrocarbon group (the hydrocarbon group having a substituent) may be a hydrocarbon group wherein at least one hydrogen atom in the above-mentioned hydrocarbon group is substituted with a substituent. The substituted hydrocarbon group include substituted alkyl, substituted aryl, substituted alkenyl, substituted alkynyl, substituted aralkyl, and the like.

The substituted heterocyclic group (the heterocyclic group having a substituent) may be a heterocyclic group wherein at least one hydrogen atom in the above-mentioned heterocyclic group is substituted with a substituent. The substituted heterocyclic group includes a substituted aliphatic heterocyclic group and a substituted aromatic heterocyclic group.

The substituent in the substituted hydrocarbon group and substituted heterocyclic group includes a hydrocarbon group, a heterocyclic group, an alkoxy group, an aryloxy group, an aralkyloxy group, an alkoxycarbonyl group, an aryloxycarbonyl group, an aralkyloxycarbonyl group, an acyl group, an acyloxy group, an alkylthio group, an aralkylthio group, an arylthio group, a halogen atom, a halogenated hydrocarbon group, an alkylenedioxy group, an amino group, a substituted amino group, a cyano group, a nitro group, a hydroxy group, an carboxy group, a sulfo group, a sulfonyl group, a substituted silyl group, and the like.

The hydrocarbon group and the heterocyclic group as the substituent are the same as the respective groups described in the above-mentioned formula (1). The halogen atom, the halogenated hydrocarbon group, the alkoxy, the aryloxy group, the aralkyloxy group and the substituted amino group are also the same as the respective groups described as the substituent in the above-mentioned formula (1). The acyl group, the alkoxycarbonyl group, the aryloxycarbonyl group, the aralkyloxycarbonyl group and the sulfonyl group are the same as the respective groups described as the substituent of the amino group in the substituted amino group as the substituent in the above-mentioned formula (1).

The acyloxy group as the substituent includes, for example, an acyloxy group derived from a carboxylic acid such as an aliphatic carboxylic acid or an aromatic carboxylic acid and having 2 to 18 carbon atoms. Specific examples thereof include, for example, acetoxy, propionyloxy, butyryloxy, pivaloyloxy, pentanoyloxy, hexanoyloxy, lauroyloxy, stearoyloxy, benzoyloxy, and the like.

The alkylthio group may be linear, branched or cyclic, and includes, for example, an alkylthio group having 1 to 6 carbon atom(s). Specific examples thereof include, for example, methylthio, ethylthio, n-propylthio, 2-propylthio, n-butylthio, 2-butylthio, isobutylthio, tert-butylthio, pentylthio, hexylthio, cyclohexylthio, and the like.

The arylthio group includes, for example, an arylthio group having 6 to 14 carbon atoms. Specific examples thereof include, for example, phenylthio, naphthylthio, and the like.

The aralkylthio group includes, for example, an aralkylthio group having 7 to 15 carbon atoms. Specific examples thereof include, for example, benzylthio, 2-phenethylthio, and the like.

In the case that the substituent is an alkylenedioxy group, for example, two adjacent hydrogen atoms in the aromatic ring in the above-mentioned aryl or aralkyl group are substituted with an alkylenedioxy group.

The alkylenedioxy group includes, for example, an alkylenedioxy group having 1 to 3 carbon atom(s). Specific examples thereof include, for example, methylenedioxy, ethylenedioxy, trimethylenedioxy, propylenedioxy, and the like.

The substituted silyl group includes, for example, a trisubstituted silyl group wherein three hydrogen atoms in a silyl group are substituted with substituents such as the hydrocarbon group such as the above-mentioned alkyl, aryl, and aralkyl, and the like. Specific examples thereof include, for example, trimethylsilyl, tert-butyldimethylsilyl, tert-butyldiphenylsilyl, triphenylsilyl, and the like.

Provided that, these substituents may be further substituted with the above-mentioned substituent.

Also, the ferrocenyl group in $R^{21}$ and $R^{22}$ are a group obtained by removing one hydrogen atom in ferrocene.

Further, in the formula (4), in the case that $R^{21}$ and $R^{22}$ are bonded to each other and are combined with the carbon atom in the carbonyl group therein so as to form a ring, the ring may be a monocyclic ring, a polycyclic ring and a condensed ring. Examples thereof include 4- to 8-membered aliphatic rings. These rings may have —O—, —NH— or the like in the carbon chain which constitutes the ring.

Specific examples of the ring, in the case that $R^{21}$ and $R^{22}$ are bonded to each other and are combined with the carbonyl group so as to form a ring, include, for example, a cyclopentanone ring, a cyclohexanone ring, a 5- to 7-membered lactone ring, a 5- to 7-membered lactam ring, and the like. These formed rings should each be a ring wherein the carbon atom in the carbonyl group in the formula (4) can become an asymmetric carbon atom by asymmetric hydrogenation.

The ketone represented by the formula (4) may be a prochiral ketone. That is, $R^{21}$ and $R^{22}$ in the formula (4) are not a hydrogen atom and $R^{21}$ and $R^{22}$ are a different group. As the result, the carbon atom to which a hydroxy group in the secondary alcohol which can be produced by reduction is bonded may become an asymmetric carbon atom. That is, the process of the present invention is characterized in that the prochiral ketone is reduced in the above-mentioned presence of the catalyst of the present invention to produce a chiral alcohol, more specifically secondary alcohol.

Specific examples of the ketone represented by the formula (4) include, for example, methyl ethyl ketone, acetophenone, benzalacetone, 1-indanone, 3,4-dihydro-(2H)-naphthalenone ferrocenyl methyl ketone, and the like, and compounds represented by the following formulae:

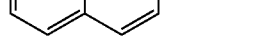
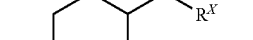

-continued

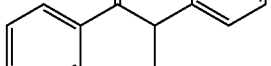
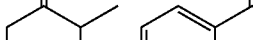
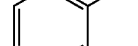
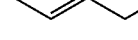
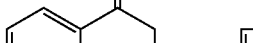
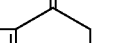
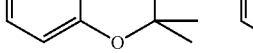
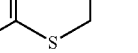

-continued

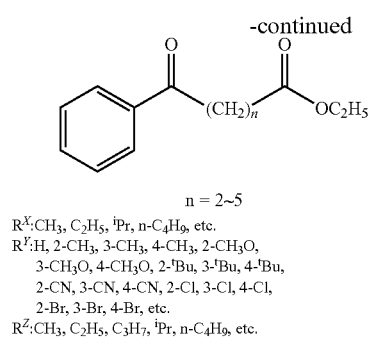

n = 2~5
$R^X$: $CH_3$, $C_2H_5$, $^iPr$, n-$C_4H_9$, etc.
$R^Y$: H, 2-$CH_3$, 3-$CH_3$, 4-$CH_3$, 2-$CH_3O$,
3-$CH_3O$, 4-$CH_3O$, 2-$^tBu$, 3-$^tBu$, 4-$^tBu$,
2-CN, 3-CN, 4-CN, 2-Cl, 3-Cl, 4-Cl,
2-Br, 3-Br, 4-Br, etc.
$R^Z$: $CH_3$, $C_2H_5$, $C_3H_7$, $^iPr$, n-$C_4H_9$, etc.

The optically active alcohol represented by the above-mentioned formula (5), which is obtained by the production process of the present invention, is an optically active secondary alcohol. Specific examples thereof include optically active alcohols derived from the compounds exemplified as the specific examples of the ketone represented by the above-mentioned formula (4), 2-butanol, phenethyl alcohol, and the like.

The process for producing an optically active secondary alcohol of the present invention, that is, the asymmetric reduction of the ketone represented by the above-mentioned formula (4) can be conducted in the presence of the catalyst for asymmetric synthesis of the present invention by a method which is known in itself.

The catalyst for asymmetric synthesis of the present invention may be a catalyst for asymmetric synthesis comprising the optically active transition metal-diamine complex (2) produced as described above, and/or the catalyst for asymmetric synthesis comprising the optically active diamine compound (1) and a transition metal compound (3). Asymmetric reduction using the latter catalyst for asymmetric synthesis is what is called in situ reaction.

The asymmetric reduction, in the case of conducting the asymmetric reduction by use of the above-mentioned optically active transition metal-diamine complex (2), can be conducted by, for example, the method described in Angewandt Chemie Int. Ed. Engl., 36, No. 3, 288 (1997) or other documents. The description in Angewandt Chemie Int. Ed. Engl., 36, No. 3, 288 (1997) is incorporated into the present specification by referring thereto.

Also, the asymmetric reduction, in the case of conducting the asymmetric reduction in situ by use of the catalyst for asymmetric synthesis comprising an optically active diamine compound (1) and the transition metal compound (3), can be conducted by, for example, a method described in J. Am. Chem. Soc., vol. 118, 4916-4917 (1996) or other documents. The description in J. Am. Chem. Soc., vol. 118, 4916-4917 (1996) is incorporated into the present specification by referring thereto.

In the case of preparing an active catalyst in situ and then conducting the asymmetric reduction, it is able to use a reaction mixture obtained by heating and stirring the optically active diamine compound (1) and the transition metal compound (3) beforehand for one to several hours.

The amount of the catalyst for asymmetric synthesis used is appropriately selected usually from the range of $10^{-1}$ to $10^{-4}$ equivalents, preferably $10^{-2}$ to $10^{-3}$ equivalents to that of the ketone.

This process of the present invention is further characterized by using the water-soluble catalyst. Accordingly, the process of the present invention can be conducted in water as a solvent or a solvent containing water. However, water is not necessarily contained. For example, an organic insoluble catalyst in water is used to conduct the reaction, water is added after the reaction to the reaction mixture, and then the water-soluble catalyst transferred to the water phase can be recovered. Preferred examples of the process include the reaction in an aqueous solution, and the reaction in a water-containing solvent.

The process for producing the optically active alcohol of the present invention is preferably conducted by using water as a solvent. When the reaction is conducted in the water solvent, the resultant secondary alcohol can easily be separated from the water layer containing the optically active transition metal-diamine complex. Additionally, the water layer containing the separated optically active transition metal-diamine complex can be repeatedly used, that is, can be recycled (reused).

The amount of water used is selected, under consideration of the kind and the solubility of the ketone, which is a reactant, economical efficiency, and others, and is appropriately selected usually from the range of 5 to 50 times, preferably that of 10 to 40 times the mass to that of the reactant.

The process for producing an optically active secondary alcohol of the present invention may be combined with water and an organic solvent if necessary in accordance with the kind of the used ketone, and others.

The used organic solvent includes aromatic hydrocarbons such as benzene, toluene and xylene; aliphatic hydrocarbons such as pentane, hexane, heptane and octane; halogenated hydrocarbons such as dichloromethane, chloroform, carbon tetrachloride and 1,2-dichloroethane; ethers such as diethyl ether, diisopropyl ether, tert-butyl methyl ether, dimethoxyethane, tetrahydrofuran, 1,4-dioxane and 1,3-dioxolane; alcohols such as methanol, ethanol, 2-propanol, n-butanol, tert-butanol and benzyl alcohol; polyhydric alcohols such as ethylene glycol, propylene glycol, 1,2-propanediol and glycerin; amides such as N,N-dimethylformamide and N,N-dimethylacetoamide; acetonitrile; N-methylpyrrolidone; dimethylsulfoxide; and the like. These solvents may be used alone or in an appropriate combination of two or more thereof.

The amount of the organic solvent used is appropriately selected usually from the range of 1 to 10 times, preferably that of 2 to 5 times the volume to the weight of the used ketone.

The reaction temperature is appropriately selected usually from the range of 15 to 100° C., preferably 20 to 80° C. under consideration of economical efficiency and others. Usually, it is desired to conduct the reaction at a relatively low temperature.

The reaction time is naturally varied in accordance with the kind or the amount of the used catalyst for asymmetric hydrogenation, the kind or the concentration of the used ketone compound, reaction conditions such as the reaction temperature, and so on. The time may be from about several minutes to several tens hours, and is appropriately selected usually from the range of 4 to 48 hours, preferably that of 6 to 24 hours.

The process for producing an optically active alcohol of the present invention can be carried out whether the reaction system is a batch system or a continuous system.

The process for producing an optically active secondary alcohol of the present invention, that is, the asymmetric reduction of the ketone represented by the formula (4) is conducted by, for example, hydrogenation (catalytic reduction) using molecular hydrogen or transfer hydrogenation using a hydrogen donator.

The hydrogenation (catalytic reduction) using molecular hydrogen can be conducted by contacting the molecular hydrogen and a reaction mixture into contact with each other under ordinary pressure or increased pressure in accordance with a known method. The catalyst comprising the optically active transition metal-diamine mixture of the present invention or the complex thereof can be used as a homogeneous catalyst or as a heterogeneous catalyst.

Also, the transfer hydrogenation using the hydrogen donator is conducted in the presence of a hydrogen donating material in the reaction system. The hydrogen donating material may be an organic compound and/or an inorganic compound, and can donate hydrogen by, for example, thermal action, the adjustment of the pH, or catalytic action in the reaction system.

The hydrogen donating material include, for example, formic acid or salts thereof, the combination of formic acid with a base, hydroquinone, phosphorous acid, an alcohol, and the like. Of these, particularly preferred are formic acid or salts thereof, the combination of formic acid with a base, an alcohol, and the like.

The salts of formic acid in formic acid or salts thereof include metal salts of formic acid such as alkali metal salts of formic acid and alkaline earth metal salts of formic acid, an ammonium salt thereof, substituted amine salts thereof, and the like.

Also, the combination of formic acid with a base may be a combination wherein formic acid will be into the form of a salt of formic acid or will be into the form of a substantial salt of formic acid in the reaction system.

The alkali metal which is combined with formic acid to form a salt include lithium, sodium, potassium, rubidium, caesium, and the like. Also, the alkaline earth metal includes magnesium, calcium, strontium, barium, and the like.

The base which forms metal salts of formic acid such as the alkali metal salts and alkaline earth metal salts of formic acid, an ammonium salt thereof, a substituted amine salt, and the base in the combinations of formic acid with the base include ammonia, an inorganic base, an organic bases, and the like.

The inorganic base include, for example, alkali or alkaline earth metal salts such as potassium carbonate, potassium hydroxide, lithium hydroxide, sodium hydrogencarbonate, sodium carbonate, potassium hydrogencarbonate, sodium hydroxide, magnesium carbonate and calcium carbonate; metal hydrides such as sodium hydride, sodium borohydride and lithium aluminum hydride, and the like.

The organic base include, for example, alkali metal alkoxides such as potassium methoxide, sodium methoxide, lithium methoxide, sodium ethoxide, potassium isopropoxide, potassium tert-butoxide, and potassium naphthalenide; acetate salts of an alkali-alkaline earth metal such as sodium acetate, potassium acetate, magnesium acetate, and calcium acetate; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, and N-methylmorpholine, organic metal compounds such as methylmagnesium bromide, ethylmagnesium bromide, propylmagnesium bromide, methyllithium, ethyllithium, propyllithium, n-butyllithium and tert-butyllithium, quaternary ammonium salts, and the like.

The alcohol as the hydrogen donating material include preferably a lower alcohol having a hydrogen atom at the a-position thereof. Specific examples thereof include, for example, methanol, ethanol, n-propanol, isopropanol, n-butanol, sec-butanol, and the like. Of these, isopropanol is preferred.

In the process for producing an optically active secondary alcohol of the present invention, it is desired to conduct asymmetric hydrogenation in an aqueous solvent, as will be described later. Therefore, the used hydrogen donating material is preferably a water-soluble material. Among them, considering reactivity and economical efficiency, preferred are alkali metal salts, alkaline earth metal salts, an ammonium salt and substituted amine salts of formic acid.

The amount of the hydrogen donating material used is appropriately selected usually from the range of 2 to 20 equivalents, preferably the range of 4 to 10 equivalents to that of the ketone. When the water layer remaining subsequently to the separation of the product after the reaction is reused, the salt of formic acid, which is a hydrogen source consumed in the reaction, may be replenished if necessary.

In the process for producing an optically active alcohol of the present invention, the catalyst for asymmetric reduction used for the asymmetric reduction can be recovered in the form of an aqueous solution and then used. In the same manner, the catalyst for asymmetric synthesis of the present invention can be recovered in the form of an aqueous solution thereof after the end of the asymmetric synthesis reaction. That is, the catalyst for asymmetric synthesis of the present invention can easily be recycled (reused).

The recovery of the catalyst for asymmetric synthesis or the aqueous solution thereof can be conducted by a known operation such as liquid separation, extraction, and the like from the reaction mixture (the reaction system).

For example, after the end of the asymmetric synthesis reaction such as the asymmetric reduction and the like, the aqueous solution of the catalyst for asymmetric synthesis can be recovered by, if necessary, adding an organic solvent or water into the reaction solution to prepare two layers, and separating the water layer from this reaction solution which are in the two layers.

The recovered aqueous solution of the catalyst for asymmetric synthesis can be reused (recycled), as it is, for the same asymmetric synthesis reaction without conducting especial post-treatment, purification or the like. Also, if necessary, this separated water layer is subjected to an operation such as concentration, purification, and the like, whereby the catalyst for asymmetric synthesis can easily be recovered.

At the time of separating the water layer after the end of the asymmetric synthesis reaction, such as asymmetric reduction and the like, which is performed in the aqueous solvent, the organic solvent used if necessary may be any solvent which can be phase separated from water. Specific examples thereof include, for example, aliphatic hydrocarbons such as pentane, hexane, heptane, octane, decane and cyclohexane; aromatic hydrocarbons such as benzene, toluene and xylene; ethers such as diethyl ether, diisopropyl ether, tert-butyl methyl ether, dimethoxyethane, ethylene glycol diethyl ether, tetrahydrofuran, 1,4-dioxane and 1,3-dioxolane; ketones such as acetone, methyl ethyl ketone, methyl isobutyl ketone and cyclohexanone; halogenated hydrocarbons such as dichloromethane, 1,2-dichloroethane, chloroform, carbon tetrachloride and o-dichlorobenzene; esters such as methyl acetate, ethyl acetate, n-butyl acetate and methyl propionate; and the like. These organic solvents may be used alone or in an appropriate combination of two or more thereof.

The recovered catalyst for asymmetric synthesis of the present invention, also, can be reused for the same asymmetric synthesis reaction or the same kind of asymmetric synthesis reaction after the catalyst is subjected to post-treatment, purification and the like if necessary, and can also be used for other asymmetric synthesis reaction. For example, the catalyst for asymmetric synthesis of the present invention used for transfer hydrogenation can be recovered, purified if necessary, and then used for other hydrogenation.

In the case of reusing (recycling) the recovered catalyst for asymmetric synthesis of the present invention or the aqueous solution thereof, it is optional to carry out an appropriate adjustment of the amount of the catalyst for asymmetric synthesis, for example, optional addition of a new catalyst for asymmetric synthesis.

Thus obtained optically active secondary alcohol is used as a medicine intermediate, a liquid crystal material or the like.

The optically active transition metal-diamine complex of the present invention is characterized by having, as a ligand, an optically active diamine complex having a substituted amino group in its phenyl group. In this manner, the above-mentioned optically active transition metal-diamine complex becomes water-soluble. Therefore, in the case that said complex, for example, as a catalyst for asymmetric synthesis, in particular, a catalyst for asymmetric reduction is conducted to an asymmetric reduction such as an asymmetric hydrogenation or an asymmetric transfer hydrogenation by use thereof, said catalyst is able to be recycled, which leads to reduction in cost. Further, such asymmetric synthesis reaction can be conducted in an aqueous solvent, and the catalyst can be very easily separated or recovered. Therefore, it can be said that the catalyst for asymmetric synthesis of the present invention is considered environment-friendly.

BEST MODE FOR CARRYING OUT OF THE INVENTION

EXAMPLES

The present invention will hereinafter be more specifically described by the following examples, however, the present invention is not limited thereto.

In the following examples, devices used to measure physical properties are as follows:
1) Gas chromatography (GLC): Hewlett Packard 5890-II
2) Specific rotation: JASCO, DIP-360 type Specific Rotation Meter
3) $^1$H-NMR, $^{13}$C-NMR: DRX-500, manufactured by Buruker Co.
4) High-Performance Liquid Chromatography (HPLC): Shimadzu Corp. LC10AT & SPD10A

Example 1

Synthesis of 1,2-di(4-N,N-dimethylaminophenyl) ethylene-1,2-diamine (1) Synthesis of di 4-N,N-dimethylbenzoazine To a mixed solution of 10.4 g (0.08 mol) of hydrazine sulfate and 78 mL of water was added 8.9 g (0.1464 mol) of 28% ammonia water, and the resultant solution was heated. Next, to this solution was dropwise added 80 mL of tetrahydrofuran (THF) solution of a 26.76 g (0.179 mol) of 4-N,N-dimethylaminobenzaldehyde at 40° C. or lower taking 2 hours or more, and the solution was further reacted with stirring at the same temperature for 2 to 3 hours. To the reaction solution was added 28% ammonia water to make the water layer alkaline. Thereafter, 100 mL of toluene was added thereto and the resultant was cooled to 10° C. The precipitated yellow solid substance was filtrated off, and was washed with toluene and water in sequence. In addition, the solid substance obtained from the organic layer of the filtrate was washed with water and toluene in sequence. The solid substances are joined and was azeotropically dehydrated in toluene to give 23.36 g of crude di4-N,N-dimethylaminobenzoazine. The resultant 23.36 g of crude di4-N,N-dimethylaminobenzoazine was dissolved in 1600 mL of THF under heating and reflux. The resultant solid substance was filtrated in thermal state and was allowed to stand overnight at 5° C. Thereafter, the precipitated crystal was filtrated off, and dried to give 19.75 g of purified di4-N,N-dimethylaminobenzoazine. Yield: 83.97%. HPLC content: 98.04%. mp: 265-266° C.

(2) Synthesis of (1R,2R)-1,2-di(4-N,N-dimethylaminophenyl)ethylene-1,2-diamine

Under the nitrogen atmosphere, 28.45 g (0.15 mol) of titanium tetrachloride was dropwise added to a solution wherein 19.62 g (0.3 mol) of zinc powder and 300 mL of THF were mixed at −40° C. or lower taking 40 minutes. The solution was reacted with stirring at the same temperature for 30 minutes, and was further reacted with stirred at −30 to −25° C. for 1 hour. And then, to this reaction solution was added 8.82 g (0.03 mol) of di4-N,N-dimethylaminobenzoazine at −25° C., and the solution was reacted with stirring for 3 hours as being restored to room temperature. After the resultant was allowed to stand overnight, the reaction solution was poured into 300 g of dilute hydrochloric acid (30 g of concentrated hydrochloric acid, and 270 g of water). The precipitated solid substance was filtrated off (dry weight of said solid substance: 9.31 g), and THF was recovered from the filtrate. The residue was washed with dichloromethane two times. The water layer was neutralized with a 20% solution of NaOH in water to make a strong alkaline (pH>11), and then was subjected to extraction with 600 mL of THF. The organic layer was washed with saturated brine three times, dried over anhydrous magnesium sulfate, and concentrated under reduced pressure to distill off THF, thereby giving 6.78 g of crude 1,2-di(4-N,N-dimethylaminophenyl)ethylene-1,2-diamine.

To a mixed solution of 3.48 g (11.68 mmol) of obtained crude 1,2-di(4-N,N-dimethylaminophenyl)ethylene-1,2-diamine and 25 mL of methanol was dropwise added 4.9 g (49 mmol) of concentrated hydrochloric acid under cooling. The solution was stirred and then concentrated under reduced pressure to distill off methanol and water, thereby giving 4.6 g of a crude hydrochloride salt of 1,2-di(4-N,N-dimethylaminophenyl)ethylene-1,2-diamine. The resultant crude hydrochloride salt of 1,2-di(4-N,N-dimethylaminophenyl)ethylene-1,2-diamine was washed with 20 mL of ethanol, filtrated off, and dried to give 2.66 g of a hydrochloride salt of 1,2-di (4-N,N-dimethylaminophenyl)ethylene-1,2-diamine (yellowish white fine powder solid).

Next, to the resultant hydrochloride salt of 1,2-di(4-N,N-dimethylaminophenyl)ethylene-1,2-diamine was added an aqueous solution containing 0.923 (23.08 mmol) of sodium hydroxide and 20 mL of water to neutralize the salt. Thereafter, an aqueous solution of sodium hydroxide was further added thereto so as to make the aqueous solution a strong alkaline. The fine powder liberated from the water layer was filtrated off, washed with water, and dried under reduced pressure to give 1.04 g of a crude racemic form of 1,2-di(4-N,N-dimethylaminophenyl)ethylene-1,2-diamine. mp=106-106.5° C. HPLC content: 61.9% [a Chiralcel OD-H column (Daicel Chemical Industries, Ltd.) was used].

The resultant racemic form of 1,2-di(p-4-N,N-dimethylaminophenyl)ethylene-1,2-diamine was made into a 1% solution thereof in ethanol. The racemic form was purified by high-performance liquid chromatography [a Chiralcel OD-H column (manufactured by Daicel Chemical Industries, Ltd.) was used. elute: 25 parts of ethanol+75 parts of n-hexane], so as to give 112 mg of 1,2-di(4-N,N-dimethylaminophenyl)

ethylene-1,2-diamine having a purity of 79.2%. The contents by percentage of both enantiomers thereof were the (1S,2S) form is 6.96%, and the (1R,2R) form is 82.88% (the meso form: 4.11%). This was further purified under the same conditions, so as to give 63.1 mg of 1,2-di(4-N,N-dimethylaminophenyl)ethylene-1,2-diamine containing the (1R,2R) form excess, wherein the HPLC purity was (1S,2S) form is 5.03%, and (1R,2R) form is 91.8% (meso form: 0.24%).

Mp=133-134° C.
$[a]_D^{20}$=+98.2 (C=1, ethanol)
$^1$H NMR (CD$_3$OD, 500 MHz):
2.77 (12H, s), 3.83 (2H, s), 6.57 (4H, d, 11.7), and 6.9 (4H, d, 11.7)
MS (ionizing method APCI+, m/z): 282.2 (M$^+$-NH$_2$)

Example 2

Synthesis of Monobenzenesulfamide of (1R,2R)-1,2-di(4-N,N-dimethylaminophenyl)ethylene-1,2-diamine To a mixed solution of 50 mg (0.167 mmol) of (1R,2R)-1,2-di(4-N,N-dimethylaminophenyl)ethylene-1,2-diamine obtained in Example 1, 17.7 mg (0.1752 mmol) of triethylamine and 1 mL of dichloromethane was added a solution of 28.1 mg (0.1593 mmol) of benzenesulfonyl chloride in 1 mL of dichloromethane in such a manner that at intervals of 15 minutes a volume of 0.05 mL was added at each time under cooling with ice. Thereafter, the solution was further reacted with stirring at the same temperature. The reaction solution was poured into water to terminate the reaction. Thereafter, sodium carbonate was added thereto to make the solution alkaline. And then, the dichloromethane layer was separated, washed with water, dried over anhydrous magnesium sulfate, and then concentrated to give 73.9 mg of crude monobenzenesulfamide of (1R,2R)-1,2-di(4-N,N-dimethylaminophenyl)ethylene-1,2-diamine. HPLC content: the (1R,2R) form, 85.65%.

A TLC plate (silica gel) was used and THF was used as a solvent to separate the resultant crude monobenzenesulfamide of (1R,2R)-1,2-di(4-N,N-dimethylaminophenyl)ethylene-1,2-diamine. Thereafter, the crude product was extracted with THF and methanol to give 57.4 mg of purified monobenzenesulfamide of (1R,2R)-1,2-di(4-N,N-dimethylaminophenyl)ethylene-1,2-diamine. HPLC content: the (1R,2R) form, 90.3%, and the (1S,2S) form, 2.2%.

mp: 164-165° C.
$^1$H NMR (CD$_3$OD, 500 MHz):
2.68 (6H, s), 2.74 (6H, s), 3.85 (1H, d, 9.1), 4.22 (1H, d, 9.1), 6.24 (2H, d, 8.7), 6.47-6.50 (5H, dd, 8.9), 6.85 (2H, d, 8.8), 7.14 (2H, t, 7.6), 7.27 (1H, t, 7.6), and 7.4 (2H, d, 7.6)
MS (ionizing method APCI+, m/z): 422.4 (M$^+$−16), 461.4 (M$^+$+23)

Example 3

Transfer hydrogenation of acetophenone using monobenzenesulfamide of (1R,2R)-1,2-di(4-N,N-dimethylaminophenyl)ethylene-1,2-diamine and [RuI$_2$(mesithylene)]$_2$ To a mixed solution of 4 mg (0.0098 mmol) of monobenzenesulfamide of (1R,2R)-1,2-di(4-N,N-dimethylaminophenyl)ethylene-1,2-diamine, 1.86 mg (0.0032 mmol) of [RuCl$_2$(mesithylene)]$_2$, 0.45 mg (6.7 mmol) of sodium formate, and 4 mL of water was added 0.2 g (1.66 mmol) of acetophenone, and the solution was reacted with stirring at 50° C. for 2.5 hours. As a result, it was confirmed that an alcohol was given with a conversion ratio of 97.9% and a selection ratio of 99.62%.

The pH of the water layer was 8.4 at the time of the end of the reaction. To the reaction solution was added 76.4 mg (1.66 mmol) of formic acid to make the solution into an acidity (pH=5.5). Thereafter, the product was extracted with heptane (the separated water layer was reused in the next reaction). The heptane extracted solution was washed with water, dried over anhydrous magnesium sulfate, and concentrated to give 0.19 g of (1R)-phenethyl alcohol (OP=90.78% ce).

Example 4

Reuse of the Water Layer in Example 3

In Example 3, 0.2 g (1.66 mmol) of acetophenone was added to the water layer which was recovered after the end of the reaction, and the solution was reacted with stirring at 50° C. for 16 hours. As a result, it was confirmed that an alcohol was given with a conversion ratio of 88.7% and a selection ratio of 100%. The pH was 8.85 at the end of the reaction. After the end of the reaction, post-treatment was conducted in the same way as in Example 3, so as to give 0.19 g of (1R)-phenethyl alcohol (OP=87.7%).

Example 5

Transfer hydrogenation of acetophenone using monobenzenesulfamide of (1R,2R)-1,2-di(4-N,N-dimethylaminophenyl)ethylene-1,2-diamine and [Cp*RhCl$_2$]$_2$ To a mixed solution of 4 mg (0.0098 mmol) of monobenzenesulfamide of (1R,2R)-1,2-di(4-N,N-dimethylaminophenyl)ethylene-1,2-diamine, 1.98 mg (0.0032 mmol) of [Cp*RhCl$_2$]$_2$, 0.45 mg (6.7 mmol) of sodium formate, and 4 mL of water was added 0.2 g (1.66 mmol) of acetophenone, and the solution was reacted with stirred at 50° C. for 4 hours. As a result, it was confirmed that an alcohol was given with a conversion ratio of 92.34% and a selection ratio of 100%. The pH was 8.85 at the time of the end of the reaction. After the end of the reaction, post-treatment was conducted in the same way as in Example 3, so as to give 0.19 g of (1R)-phenethyl alcohol (OP=92.4% ee).

INDUSTRIAL APPLICABILITY

The transition metal-optically active diamine mixture of the present invention which comprises the optically active diamine compound of the present invention, or the optically active complex thereof is useful as various catalysts for asymmetric synthesis, in particular, catalysts for asymmetric reductions, especially, a catalyst for transfer hydrogenation. For example, when a prochiral ketone is subjected to asymmetric reduction, the corresponding optically active alcohol can be obtained with a high yield and a good optical purity. Also, the optically active transition metal-diamine complex catalyst of the present invention is water-soluble and can be used as a homogeneous system in an aqueous solvent. For this reason, after the reaction the catalyst can easily be separated from the reaction product by liquid separation or the like, and can be recovered or reused. Thus, environment pollution resulting from the transition metal or the organic material can be prevented.

Accordingly, the present invention is very industrially useful since the present invention provides a novel catalyst for asymmetric synthesis and further the present invention provides a catalyst for organic synthesis which is environmentally friendly.

What is claimed is:

1. An optically active transition metal-diamine complex represented by the formula (2):

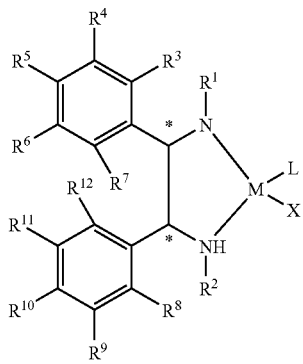

(2)

wherein $R^1$ and $R^2$ each independently represent a hydrogen atom, an optionally substituted hydrocarbon group, or —$SO_2R^{13}$ (wherein $R^{13}$ represents an optionally substituted hydrocarbon group, a camphoryl group, or a substituted amino group), $R^3$ to $R^{12}$ each independently represent a hydrogen atom, an optionally substituted hydrocarbon group, an optionally substituted heterocyclic group, an optionally substituted alkoxy group, an optionally substituted aryloxy group, an optionally substituted aralkyloxy group, or a substituted amino group, M represents ruthenium, X represents a halogen atom, L represents a benzene which may be substituted with an alkyl group, and * represents an asymmetric carbon atom, provided that at least one of $R^3$ to $R^7$ and $R^8$ to $R^{12}$ is a substituted amino group.

2. An optically active transition metal-diamine complex obtained by reacting an optically active diamine compound represented by the formula (1):

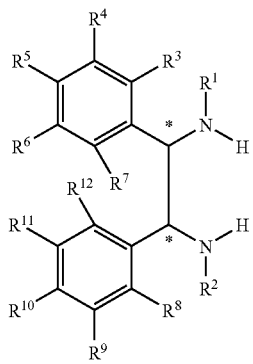

(1)

wherein $R^1$ and $R^2$ each independently represent a hydrogen atom, an optionally substituted hydrocarbon group, or —$SO_2R^{13}$ (wherein $R^{13}$ represents an optionally substituted hydrocarbon group, a camphoryl group, or a substituted amino group), $R^3$ to $R^{12}$ each independently represent a hydrogen atom, an optionally substituted hydrocarbon group, an optionally substituted heterocyclic group, an optionally substituted alkoxy group, an optionally substituted aryloxy group, an optionally substituted aralkyloxy group, or a substituted amino group, and * represents an asymmetric carbon atom, provided that at least one of $R^3$ to $R^7$ and $R^8$ to $R^{12}$ is a substituted amino group; and a transition metal compound represented by the formula (3):

$$[MX_mL_n]_p \qquad (3)$$

wherein M represents ruthenium, X represents a halogen atom, L represents a benzene which may be substituted with an alkyl group, m represents 2, n represents 1, and p represents 2.

3. A catalyst for asymmetric synthesis comprising the optically active transition metal-diamine complex according to claim 1 or 2.

4. The catalyst for asymmetric synthesis according to claim 3, wherein the catalyst for asymmetric synthesis is a catalyst for asymmetric reduction.

5. A catalyst for asymmetric synthesis comprising an optically active diamine compound represented by the formula (1):

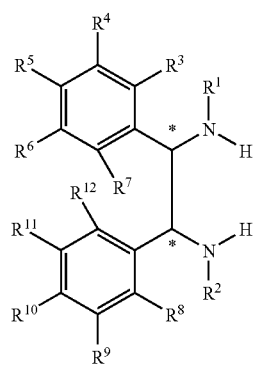

(1)

wherein $R^1$ and $R^2$ each independently represent a hydrogen atom, an optionally substituted hydrocarbon group, or —$SO_2R^{13}$ (wherein $R^{13}$ represents an optionally substituted hydrocarbon group, a camphoryl group, or a substituted amino group), $R^3$ to $R^{12}$ each independently represent a hydrogen atom, an optionally substituted hydrocarbon group, an optionally substituted heterocyclic group, an optionally substituted alkoxy group, an optionally substituted aryloxy group, an optionally substituted aralkyloxy group, or a substituted amino group, and * represents an asymmetric carbon atom, provided that at least one of $R^3$ to $R^7$ and $R^8$ to $R^{12}$ is a substituted amino group; and a transition metal compound represented by the formula (3):

$$[MX_mL_n]_p \qquad (3)$$

wherein M represents ruthenium, X represents a halogen atom, L represents a benzene which may be substituted with an alkyl group, m represents 2, n represents 1, and p represents 2.

6. The catalyst for asymmetric synthesis according to claim 5, wherein the catalyst for asymmetric synthesis is a catalyst for asymmetric reduction.

7. A process for producing an alcohol, which comprises subjecting a ketone to an asymmetric reduction in an aqueous solvent in the presence of the catalyst for asymmetric reduction of claim 4 or 6.

8. The process according to claim 7, wherein the ketone is a prochiral ketone, and the produced alcohol is an optically active alcohol.

9. The process according to claim 8, wherein the ketone is a ketone represented by the following formula (4):

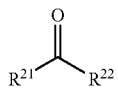

(4)

wherein $R^{21}$ and $R^{22}$ each independently represent an optionally substituted hydrocarbon group, an optionally substituted heterocyclic group, or a ferrocenyl group, provided that $R^{21} \neq R^{22}$, and $R^{21}$ and $R^{22}$ may be bonded to each other to form a cyclic ketone having a substituent, and the resultant optically active alcohol is an optically active alcohol represented by the following formula (5):

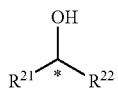

(5)

wherein * represents an asymmetric carbon atom and $R^{21}$ and $R^{22}$ are the same as described above.

10. The process according to claim 7, wherein the asymmetric reduction is based on asymmetric transfer hydrogenation.

11. The process according to claim 7, wherein the catalyst for asymmetric reduction is recovered after use.

12. The process according to claim 11, wherein the recovery is performed in the form of an aqueous solution.

13. The process according to claim 7, wherein the recovered catalyst for asymmetric reduction is recycled.

14. The process according to claim 13, wherein the recovered catalyst for asymmetric reduction is a catalyst to be recycled in the form of the recovered aqueous solution.

15. A diamine compound represented by the formula (1b):

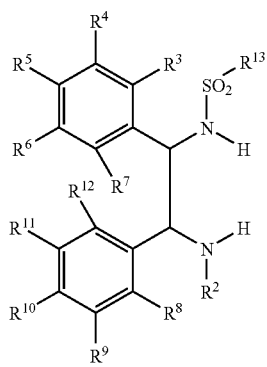

(1b)

wherein $R^2$ represents a hydrogen atom, an optionally substituted hydrocarbon group, or $-SO_2R^{13}$ (wherein $R^{13}$ represents an optionally substituted hydrocarbon group, a camphoryl group, or a substituted amino group), $R^3$ to $R^{12}$ each independently represent a hydrogen atom, an optionally substituted hydrocarbon group, an optionally substituted heterocyclic group, an optionally substituted alkoxy group, an optionally substituted aryloxy group, an optionally substituted aralkyloxy group, or a substituted amino group, and $R^{13}$ represents an optionally substituted hydrocarbon group, a camphoryl group, or a substituted amino group, provided that at least one of $R^3$ to $R^7$ and $R^8$ to $R^{12}$ is a substituted amino group.

16. The optically active transition metal-diamine complex according to claim 2, wherein the transition metal compound represented by the formula (3) is selected from the group consisting of $[RuCl_2(benzene)]_2$, $[RuBr_2(benzene)]_2$, $[RuI_2(benzene)]_2$, $[RuCl_2(p\text{-cymene})]_2$, $[RuBr_2(p\text{-cymene})]_2$, $[RuI_2(p\text{-cymene})]_2$, $[RuCl_2(hexamethylbenzene)]_2$, $[RuBr_2(hexamethylbenzene)]_2$, $[RuI_2(hexamethylbenzene)]_2$, $[RuCl_2(mesitylene)]_2$, $[RuBr_2(mesitylene)]_2$, and $[RuI_2(mesitylene)]_2$.

17. The catalyst for asymmetric synthesis according to claim 5, wherein the transition metal compound represented by the formula (3) is selected from the group consisting of $[RuCl_2(benzene)]_2$, $[RuBr_2(benzene)]_2$, $[RuI_2(benzene)]_2$, $[RuCl_2(p\text{-cymene})]_2$, $[RuBr_2(p\text{-cymene})]_2$, $[RuI_2(p\text{-cymene})]_2$, $[RuCl_2(hexamethylbenzene)]_2$, $[RuBr_2(hexamethylbenzene)]_2$, $[RuI_2(hexamethylbenzene)]_2$, $[RuCl_2(mesitylene)]_2$, $[RuBr_2(mesitylene)]_2$, and $[RuI_2(mesitylene)]_2$.

* * * * *